(12) United States Patent
Pridgeon et al.

(10) Patent No.: US 8,637,049 B2
(45) Date of Patent: Jan. 28, 2014

(54) ATTENUATED LIVE VACCINES FOR AQUATIC ANIMALS

(75) Inventors: Yuping Wei Pridgeon, Auburn, AL (US); Phillip H. Klesius, Auburn, AL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 5 days.

(21) Appl. No.: 13/081,134

(22) Filed: Apr. 6, 2011

(65) Prior Publication Data

US 2012/0258139 A1  Oct. 11, 2012

(51) Int. Cl.
*A61K 39/09* (2006.01)
*A61K 31/04* (2006.01)
*A61K 39/02* (2006.01)
*C12N 1/36* (2006.01)
*C12N 1/20* (2006.01)
*A61P 37/04* (2006.01)

(52) U.S. Cl.
USPC .............. 424/244.1; 435/252.1; 435/253.4; 435/245; 424/234.1

(58) Field of Classification Search
None
See application file for complete search history.

(56) References Cited

U.S. PATENT DOCUMENTS

| | | | |
|---|---|---|---|
| 6,019,981 A | 2/2000 | Klesius et al. | |
| 6,153,202 A | 11/2000 | Klesius et al. | |
| 7,067,122 B1 | 6/2006 | Evans et al. | |
| 2010/0221286 A1 | 9/2010 | Klesius et al. | |

OTHER PUBLICATIONS

Colman (Res. Immunology, Jan. 1994, vol. 145, pp. 33-36; e.g. p. 33, col. 2).*
Greenspan et al. (Nature Biotechnology 7: 936-937, 1999).*
Shoemaker, C.A. et al., Efficacy of a Modified Live *Edwardsiella ictaluri* Vaccine in Channel Catfish as Young as Seven Days Post Hatch, Aquaculture, 1999, 189-193, vol. 176.
Arias, C.R. et al., A Compartative Study of *Ewardsiella ictaluri* parent (EILO) and *E. ictaluri* Rifampicin-mutant (RE-33) Isolates Using Lipopolysaccharides, Outer Membrane Proteins, Fatty Acids, Biolog, API 20E and Genomic Analysis, Journal of Fish Diseases, 2003, 415-321, vol. 26.
Lawrence, M.L. et al., Attenuation, Persistence, and Vaccine Potential of an *Edwardsiella ictaluri* purA Mutant, Infection and Immunity, 1997, 4642-4651, vol. 65, No. 11.
Robson, R.L. et al., Morphological Changes Associated with Novobiocin Resistance in *Bacillus licheniformis*, Journal of Bacteriology, 1977, 1045-1050, vol. 129, No. 2.
Barrett-Bee, K. et al., A Comparision of the Accumulation of Novobiocin into Bacteria with its Antibacterial Properties, Journal of Antimicrobial Chemotherapy, 1994, 1041-1045, vol. 34.
Jones, R.N., Should Novobiocin be Clinically Re-Evaluated?, Diagn Microbiol Infect Dis, 1989, 363-365, vol. 12.
Shoemaker, C.A. et al., In ovo Methods for Utilizing the Modified Live *Edwardsiella ictaluri* Vaccine Against Enteric Septicemia in Channel Catfish, Aquaculture, 2002, 221-227, vol. 203.
Brock, T., Studies on the Mode of Action of Novobiocin, J. Bacteriol. 1956. vol. 72(3), p. 320.
Arif, M., Adaptive Acquisition of Novobiocin resistance in *Pasteurella multocida* Strains of Avian Origin, Veterinary Research Communications, 22 (1998), p. 445-455.

* cited by examiner

*Primary Examiner* — Robert A Zeman
(74) *Attorney, Agent, or Firm* — John D. Fado; David L. Marks

(57) ABSTRACT

Safe and effective live vaccines against bacteria infecting aquatic animals were created through the induction of novobiocin-resistance in liquid culture and novobiocin- and rifampicin-resistance in liquid culture.

2 Claims, 17 Drawing Sheets

ATTENUATED LIVE VACCINES FOR AQUATIC ANIMALS

BACKGROUND OF THE INVENTION

1. Field of the Invention

This invention relates to novel microorganisms and vaccines for the protection of aquatic animals from bacterial diseases such as, motile *Aeromonas* septicemia, enteric septicemia, and streptococcal diseases. This invention also relates to methods for using the novel vaccines to protect aquatic animals from bacterial disease as well as to methods for preparing the vaccines using novel antibiotic resistance strategies.

2. Description of the Related Art

Disease problems constitute the largest single cause of economic losses in aquaculture and bacterial infections constitute the most important source of disease problems in various types of production (Meyer, 1991, J. Anim Sci. Volume 69, 4201-4208). Estimated economic impact from infections caused by bacterial infection on aquaculture industry annually is at least $10 million in the USA alone and more than $100 million globally (Shoemaker et al., 2010. J. Fish Dis. Volume 33, 537-44).

Antibiotics and chemotherapeutic drugs have been used for disease management in feed additives and in direct administration into fish pond water; however, there has been an increase in drug resistant strains (Son et al., 1997, Letters in Appl. Microbiol., Volume 24, 479-482); (Harikrishnan and Balasundaram, 2005, Reviews in Fisheries Science, Volume 13, 281-320).

*Edwardsiella ictaluri* (*E. ictaluri*) causes enteric septicemia of catfish (ESC) which is the most prevalent disease affecting farm-raised catfish, *Ictalurus punctatus*. *E. ictaluri* is a facultative Gram-negative flagellated bacterium akin to phylogenetically related *Salmonella* (Thune et al., J. World Aqua Soci, Volume 28, 193-201, 1997; Zhang and Arias, Syst. Appl. Microbiol., Volume 30, 93-101, 2007). ESC is responsible for approximately $20 to $30 million in annual losses to catfish farmers in the southeastern United States (Plumb and Vinitnantharat, J. Fish. Dis., Volume 16, 65-71, 1993). ESC is generally an acute septicemia that develops very quickly, resulting in heavy mortalities at as early as 4 days after infection (Thune et al., supra; Newton et al., J. Fish. Dis., Volume 12, 335-347,1989; Wolters and Johnson, J. Aquat. Anim. Health, Volume 6, 329-334, 1994).

*Streptococcus iniae* is a significant fish pathogen impacting aquaculture production worldwide. Since its original isolation in 1976 from Amazon freshwater dolphin (*Inia geoffrensiss*) (Pier and Madin, 1976, Inyt. J. Syst. Bacteriol, Volume 26, 545-553), *Streptococcus iniae* has become a major aetiological agent of *Streptococcus* in farmed and wild finfish worldwide, affecting more than 30 species of fish, including trout, yellowtail, tilapia, barramundi, and hybrid striped bass (Cheng et al, 2010, Vaccine Volume 28, 2636-2641; Eyngor et al., 2008, Appl. Environ Microbiol., Volume 74, 6892-6897; Agnew and Barnes, 2007, Vet. Mcirobiol., Volume 122, 1-15; Ferguson et al., 2000, Vet Rec Volume 147, 662-664; Barnes, 2007, Vet Microbiol., Volume 122, 1-15; Ferguson et al., 2000, Vet Rec., Volume 147, 662-664; Bromage et al., 1999, Dis Aquat Organ, Volume 36, 177-181; Eldar et al., 1999, Dis Aquat Organ, Volume 36, 121-127). More recently, this bacterium has also been identified as a potential zoonotic pathogen, with at least 25 cases of human infection by *S. iniae* confirmed to date (Agnew and Barnes, 2007, supra; Sun et al., 2007, J. Med. Microbiol., Volume 56, 1246-1249; Koh et al., 2004, Emerg Infect Dis, Volume 10, 1694-1696; Weinstein et al., 1997, N. Engl J. Med., Volume 337, 589-594).

*Edwardsiella tarda* is a Gram-negative, motile, rod-shaped, aquatic bacterial pathogen which is highly infectious in both warm and cold water fish species. The bacterium is commonly encountered in channel catfish ponds, intensive tilapia culture, and eel production systems and is, therefore, a constant threat of disease. In the channel catfish (*Ictalurus punctatus*), *E. tarda*, the causative agent of enteric septicemia disease, has been isolated from channel catfish in areas of the southeastern United States. The disease also affects numerous other cultured fish species, sport fish, such as large-mouth bass, baitfish, and aquarium fishes. Wyatt et al. (Applied Environmental Microbiology, Volume 38, 710-714, 1979) found that in *E. tarda* positive catfish ponds, this bacterium was isolated from 75% of the pond water, 64% of pond mud, and 100% of apparently healthy frog, turtle, and crayfish samples. Meyer and Bullock (Applied Microbiology, Volume 25, 155-156, 1973) highlighted the food safety problem of *E. tarda* when they reported that 88% of dressed catfish were culture-positive for *E. tarda*. This usually results in a shut down of the processing lines until they are cleaned and disinfected because of the potential risk of human infection.

*Streptococcus agalactiae* is a Group B streptococcal bacterium that causes severe economic losses in a number of species of cultured and wild fish. This infectious bacterium is common in aquaculture facilities where fish are intensively cultured in fresh, brackish, or marine waters. The high densities of fish and the aqueous environment favor the rapid transmission of streptococcal disease. Moreover, infected cultured fish may transmit the disease to wild fish populations or infected wild fish may transmit the disease to cultured populations.

*Aeromonas hydrophila* infection results in hemorrhagic septicemia and heavy mortalities in cultured and wild fish. There is no product that has been licensed for use against the motile aeromonads within the United States (Cipiano, R. C., 2001, Revision of Fish Disease Leaflet 68, U.S. Dept. Interior, Fish and Wildlife Service Div. of Fishery Res., Washington, D.C.).

Methods to control diseases in fish include the use of chemical therapeutics such as antibiotic-medicated food (Darwish 2007, Journal of Aquatic Animal Health, Volume 19, 1-7). However, large scale use of antibiotics in aquaculture is expensive and usually ineffective because sick fish normally do not eat. Furthermore, fish have developed resistance to approved food fish antibiotics, such as oxytetracycline, florfenical, and ormethorprimsulphamethoxine (Eldar et al., Dis. Aquat. Organ., Volume 36, 121-127, 1999; Sun et al, J. Med. Microbiol., Volume 56, 1246-1249, 2007; Tu et al., 2008, Microb Drug Resist. Volume 14, 311-316; Nawaz et al., 2006, Appl. Environ. Microbiol., Volume 72, 6461-6466; Balotescu et al., 2003, Roum. Arch. Microbiol. Immunol., Volume 62, 179-189; Hatha et al., 2005, Int. J. Food Microbiol., Volume 98, 131-134,; Saavedra et al., 2004, Int. Microbiol., Volume 7, 207-211.)

Alternative methods to control fish diseases include the use of vaccines. The most extensively studied *Streptococcus iniae* vaccines are killed bacterins consisting of formalin killed bacteria cells of pathogenic *Streptococcus iniae* strains (Eldar et al, 1997, Vet. Immunol. Immunopathol., Volume 56, 175-183; Bercovier et al., 1997, Dev. Biol. Stand., Volume 90, 153-160). These formalin killed bacteria cells of *Streptococcus iniae* have been previously successfully used as vaccines to protect rainbow trout in Israel. However, recently, it has been reported that these killed vaccines are unable to protect fish from infection by other isolates (serotypes) of *Streptococcus iniae* (Bachrach et al, 2001, Appl Environ Microbiol, Volume 67, 3756-3758; Eyngor et al., 2008, Appl Environ Microbiol, Volume 74, 6892-6897). In addition to killed vaccines, live attenuated *S. iniae* strains defective in phosphglucomutase and M-like protein have been reported to offer protection against homologous *S. iniae* challenge (Locke et al., PLoS One, Volume 3, e2824, 2008; Buchanan et al., Infect. Immun., Volume 73, 6935-6944, 2005). However, it is not clear whether they offer protection against heterologous *S. iniae*.

Attenuated live bacterial vaccines such as rifampicin-resistant *Edwardsiella ictaluri* (AquaVac-ESC) and *Flavobacterium columnare* (AquaVac-COL), both licensed to Intervet/Shering-Plough, have been developed through a rifampicin-resistant strategy (Klesius and Shoemaker, 1999, Adv. Vet. Med., Volume 41, 523-537; Shoemaker et al., 2007, Vaccine, Volume 25, 1126-1131) and offer great protection against infections by *E. ictaluri* and *F. columnare*. Rifampicin works by inhibiting DNA-dependent RNA polymerase in bacterial cells by binding its beta-subunit, thus preventing transcription to RNA and subsequent translation to proteins (Schullz and Zillig, 1981, Nucleic Acids Res., Volume 9, 689-6906). This strategy relies on the ability of rifampicin to induce the appearance of rough mutants on relatively solid culture media, i.e., agar plates. It has been demonstrated that the rifampicin-resistant RE-33 strain of *E. ictaluri* was unable to cause ESC, but was able to stimulate protective immunity in catfish (Klesius and Shoemaker, Adv. Vet. Med., Volume 41, 523-537, 1999). However, it is not clear whether other antibiotics could also be used to attenuate bacteria for the purpose of novel vaccine development.

Klesius et al. (US Patent Application Publication 2010/0221286, Sep. 2, 2010) discloses a modified live rifampicin-resistant *Aeromonas hydrophila* vaccine for aquatic animals wherein the *Aeromonas hydrophila* mutants were modified by using a low initial concentration of 2.5 µg/ml rifampicin and ending at about 320 µg/ml of rifampicin after 44 passages of bacteria on relatively solid culture media, i.e., agar plates. The mutants obtained by this method were used to vaccinate fish either by intraperitoneal (IP) injection or bath immersion.

Klesius et al. (U.S. Pat. Nos. 6,019,981, Feb. 1, 2000 and 6,153,202, Nov. 28, 2000) disclose modified live rifampicin-resistant *Edwardsiella ictaluri* vaccines for aquatic animals wherein the *E. ictaluri* mutants were modified by using a low initial concentration of 5.0 µg/ml rifampicin and ending at about 320 µg/ml of rifampicin after 44 passages of bacteria on relatively solid culture media, i.e., agar plates. The mutants obtained by this method were used to vaccinate fish both post-hatch and in ovo using bath immersion.

Evans et al. (U.S. Pat. No. 7,067,122) disclose a rifampicin-resistant live vaccine against *Edwardsiella tarda*. *E. tarda* was grown on modified tryptic soy agar (TSA) plates in increasing concentrations of rifampicin starting at 10 µg/ml and ending at 320 µg/ml, increasing at 20 µg/ml increments.

Evans et al. (U.S. Pat. No. 7,204,993, Apr. 17, 2007) disclose a *Streptococcus agalactiae* vaccine prepared with killed cells of isolated β-hemolytic *Streptococcus agalactiae*.

Novobiocin, also known as albamycin or cathomycin, is a natural antibiotic produced by the actinomycete *Streptomyces niveus*, a member of the order of Actinobacteria (Kominek, 1972, Antimicrob. Agents Chemother., Volume 1, 123-134,). Novobiocin works as a natural inhibitor of bacterial DNA gyrase, resulting in bacterial cell-death (Gellert et al., 1976, Proc. Natl. Acad. Sci. USA, Volume 73, 4474-4478). DNA gyrase, an ATP-dependent enzyme that acts by creating a transient double-stranded DNA break, is essential for efficient DNA replication, transcription, and recombination by catalyzing the negative supercoiling of DNA (Mdluli and Ma, 2007, Infec. Disord. Drug Targets, Volume 7, 159-168).

While various vaccines have been developed that are effective for *Aeromonas hydrophila*, *Edwardsiella ictaluri*, *Edwardsiella tarda*, *Streptococcus agalactiae* and *Streptococcus iniae* infections of aquatic animals, there remains a need in the art for efficacious and safe vaccines for the aquaculture industry. The present invention described below includes attenuated live vaccines and provides methods for treating aquatic animals using said vaccines as well as methods for preparing live attenuated bacterial vaccines that are efficacious and safe and different from related art vaccines and methods.

SUMMARY OF THE INVENTION

It is therefore an object of the present invention to provide live attenuated bacterial vaccines.

Another object of the present invention is to provide live attenuated bacterial vaccines for aquatic animals.

Another object of the present invention is to provide live attenuated *Edwardsiella ictaluri* vaccines for aquatic animals.

A still further object of the present invention is to provide live novobiocin-resistant attenuated *Edwardsiella ictaluri* vaccines for aquatic animals.

Another object of the present invention is to provide a live attenuated novobiocin-resistant attenuated *Edwardsiella ictaluri* vaccine wherein said vaccine contains the strain of *E. ictaluri* NRRL B-50348.

Another object of the present invention is to provide live attenuated *Edwardsiella tarda* vaccines for aquatic animals.

A still further object of the present invention is to provide live coumermycin-resistant attenuated *Edwardsiella tarda* vaccines for aquatic animals.

Another object of the present invention is to provide live coumermycin-resistant attenuated *Edwardsiella tarda* vaccines wherein said vaccines contain *Edwardsiella tarda* strain NRRL B-50467 and/or NRRL B-50468.

Another object of the present invention is to provide live attenuated *Streptococcus iniae* vaccines for aquatic animals.

A still further object of the present invention is to provide a live novobiocin-resistant attenuated *Streptococcus iniae* vaccine for aquatic animals.

Another object of the present invention is to provide live novobiocin-resistant attenuated *Streptococcus iniae* vaccine wherein said vaccine contains the strain *S. iniae* NRRLB-50368.

Another object of the present invention is to provide live attenuated *Streptococcus agalactiae* vaccines for aquatic animals.

A still further object of the present invention is to provide a live coumermycin-resistant attenuated *Streptococcus agalactiae* vaccine for aquatic animals.

Another object of the present invention is to provide live coumermycin-resistant attenuated *Streptococcus agalactiae* vaccine wherein said vaccine contains the strain *S. agalactiae* NRRL B-50460.

A still further object of the present invention is to provide live attenuated *Aeromonas hydrophila* vaccines for aquatic animals wherein said *Aeromonas hydrophila* vaccines comprise *Aeromonas hydrophila* selected from the deposited strains NRRL B-50369, B-50418, B-50419 and mixtures thereof.

Another object of the present invention is to provide a method for preventing and/or reducing enteric septicemia in aquatic animals by administering at least one live attenuated *Edwardsiella* vaccine.

A further object of the present invention is to provide a method for preventing and/or reducing enteric septicemia in aquatic animals by administering at least one live attenuated *Edwardsiella* vaccine wherein said vaccine contains a strain of *Edwardsiella* selected from the group consisting of NRRL B-50348, B-50467, B-50468, and mixtures thereof.

Another object of the present invention is to provide a method for preventing and/or reducing streptococcal disease in aquatic animals by administering live attenuated *Streptococcus* vaccine.

A further object of the present invention is to provide a method for preventing and/or reducing streptococcal disease in aquatic animals by administering a live attenuated *Streptococcus* vaccine wherein said vaccine contains a strain of *Streptococcus* selected from the group consisting of NRRL B-50368, B-50460, and mixtures thereof.

Another object of the present invention is to provide a method for preventing and/or reducing motile *Aeromonas* septicemia in aquatic animals by administering a live attenuated *Aeromonas hydrophila* vaccine.

A further object of the present invention is to provide a method for preventing and/or reducing motile *Aeromonas* septicemia in aquatic animals by administering a live attenuated *Aeromonas hydrophila* vaccine wherein said vaccine contains a strain of *A. hydrophila* selected from the group consisting of NRRL B-50369, B-50418, B-50419 and mixtures thereof.

Another object of the present invention is to provide a method for preparing attenuated live bacterial vaccines using a novobiocin-resistance strategy to develop novel attenuated bacteria for use as safe, efficacious vaccines.

Another object of the present invention is to provide a method for preparing attenuated live bacterial vaccines using a strategy that includes both rifampicin-resistance and novobiocin-resistance to develop novel attenuated bacteria for use as safe, efficacious vaccines.

Further objects and advantages of the present invention will become apparent from the following description.

Deposit of the Microorganisms

*Aeromonas hydrophila* strains NRRL B-50369, NRRL B-50418, and NRRL B-50419 were deposited on May 7, 2010, Sep. 29, 2010, and Sep. 29, 2010 respectively. *Edwardsiella ictaluri* strain NRRL B-50348 was deposited on Feb. 25, 2010. *Streptococcus iniae* strain NRRL B-50368 was deposited on May 7, 2010. *Edwardsiella tarda* strains NRRL B-50467 and NRRL B-50468 were deposited on Feb. 4, 2011. *Streptococcus agalactiae* strain NRRL B-50460 was deposited Jan. 18, 2011. They were deposited under the provisions of the Budapest Treaty, on the International Recognition of the Deposit of Microorganisms for the Purposes of Patent Procedure and the Regulations there under (Budapest Treaty) with the U.S.D.A. Agricultural Research Service Patent Culture Collection, National Center for Agricultural Utilization Research, 1815 N. University Street, Peoria, Ill. 61604. Access to this deposit will be available during the pendency of the application to the Commissioner of Patents and Trademarks and persons determined by the Commissioner to be entitled thereto upon request under 37 C.F.R. 1.14 and 35 U.S.C. 122. The deposits are available as required by foreign patent laws in countries where counterparts of the subject application, or it progeny are filed. However, it is to be understood that the availability of a deposit does not constitute a license to practice the subject invention in derogation of patent rights granted by a government action. Upon allowance of any claims in the application, the Applicant(s) will maintain and will make this deposit available to the public pursuant to the Budapest Treaty.

Further, the subject isolate deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the isolates. The depositor acknowledges the duty to replace the deposits should the depository be unable to furnish a sample when requested, due to the condition of the deposits. All restrictions on the availability to the public of the subject isolate deposits will be irrevocably removed upon the granting of a patent disclosing it.

Figure 1:
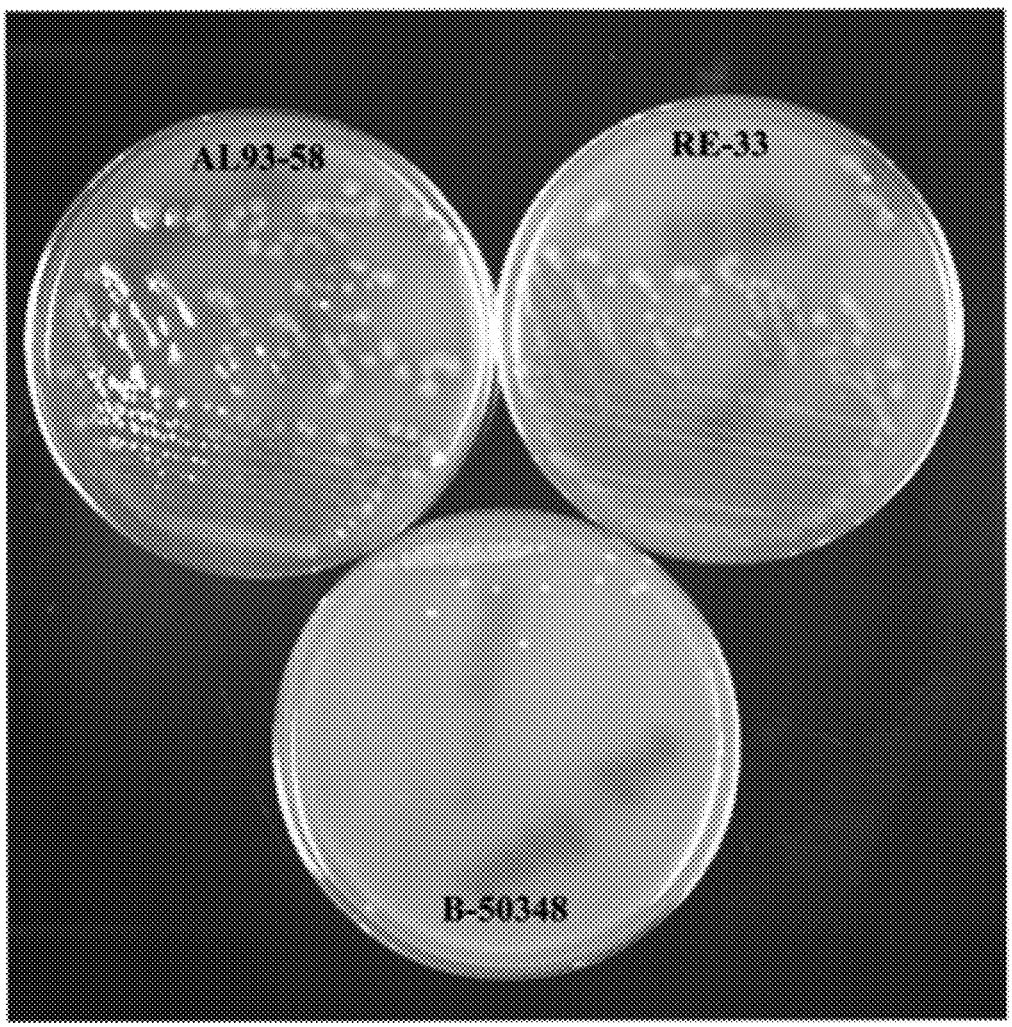
FIG. 1 is a photograph showing growth of AL93-58, RE-33, and B-50348 on 5% sheep blood agar plates. The three strains were streaked out onto 5% sheep blood agar plates and incubated at approximately 27 degrees C. for about 48 hours.

The present invention provides novel, live vaccines and methods for making and using said vaccines using any bacterium that produces a disease state in animals. More particularly, the present invention provides novel effective live vaccines and methods for making and using such vaccines for controlling diseases in aquatic animals, including, but not limited to, *Aeromonas hydrophila*, *Edwardsiella ictaluri*, *Edwardsiella tarda*, *Streptococcus agalactiae* and *Streptococcus iniae*.

DETAILED DESCRIPTION OF THE INVENTION

The vaccines disclosed in the present invention are also effective in controlling diseases caused by *Aeromonas hydrophila*, *Edwardsiella ictaluri*, *Edwardsiella tarda*, *Streptococcus agalactiae*, and *Streptococcus iniae* in a variety of fish when administered thereto. Without being limited thereto, the vaccine is especially beneficial for the treatment of tilapia (*Oreochromis* sp.), channel catfish (*I. punctutus*), American, European, and Japanese eels (*Anguilla* sp.), salmonids (*Oncorhynchus* sp. and *Salmo* sp.), striped bass and hybrid-striped bass (*Morone chrysops* X M. *saxatilis*), flounders (*Seriola* sp.), seabream (*Sparus* sp.), sea perch (*Lates calcarifer*), the estuarine grouper (*Ephinephelus tawine*), walleye (*Zander vitreum*), centrachids (such as large mouth bass, *Micropterus samoides*), bullheads (*Nebulosus* sp.), bait minnows (*Pimephales promelas*), golden shiners (*Netemigonus crysoleucas*), goldfish (*Carassius auratus*), carp (*Cyprinus carpio*) and aquarium fish species such as black mollies (*Poecilia sphenops*) and platies (*Xiphosphorus maculates*). The use of these attenuated live *Aeromonas hydrophila*, *Edwardsiella ictaluri*, *Edwardsiella tarda*, *Streptococcus agalactiae*, and *Streptococcus iniae* vaccines offer several benefits that include reducing disease loss in fresh and marine water fish and eel production, diminishing the food safety risks to humans, and reducing the contamination of water by *A. hydrophila*, *Edwardsiella ictaluri*, *Edwardsiella tarda*, *Streptococcus agalactiae*, and *Streptococcus iniae* that may be discharged in the environment from fish production systems.

Unless otherwise specified, all technical and scientific terms used herein generally have the same meaning as commonly understood by one of ordinary skill in the art to which this invention belongs.

Vaccine is defined herein in its broad sense to refer to any type of biological agent in an administrable form capable of stimulating a protective immune response in an animal inoculated with the vaccine.

Effective immunization or vaccination dose or dosage is defined herein as being the amount that will induce complete or partial immunity in a vaccinated aquatic animal against a subsequent challenge by a virulent strain.

Relative percent survival (RPS) is a measure of protection following experimental challenge as described by Amend (Dev. Bio. Stand., Volume 49, 447-454, 1981; which is herein incorporated by reference in its entirety). RPS is calculated according to the formula: RPS=(1−vaccinate mortality÷control mortality)×100. A positive vaccine effect is indicated by a RPS equal or greater than about 60%.

Efficacious vaccine is defined herein as a vaccine that offers equal or greater than about 60% protection against pathogen infections.

Rifampicin, also known as rifampin, is a bactericidal antibiotic drug of the rifamycin group. It is a semisynthetic compound derived from *Amycolatopsis rifamycinica* (formerly known as *Amycolatopsis mediterranei* and *Streptomyces mediterranie*).

Rifampicin-resistant strategy is defined as a strategy that uses rifampicin to induce rifampicin resistance in bacteria. Rifampicin works by inhibiting DNA-dependent RNA polymerase in bacterial cells by binding it beta-subunit, thus preventing transcription to RNA and subsequent translation to proteins.

Novobiocin, also known as albamycin or cathomycin, is an aminocoumarin antibiotic that is produced by the actinomycete *Streptomyces niveus*, which has recently been identified as a subjective synonym for *Streptomyces spheroids*, a member of the order Actinobacteria. Novobiocin also includes novobiocin-like chemicals including for example, coumermycin.

Novobiocin-resistance strategy is defined as a strategy that uses novobiocin or a novobiocin-like chemical, such as coumermycin, to induce novobiocin resistance in bacteria. Novobiocin and novobiocin-like chemicals are natural inhibitors of bacterial DNA gyrase.

Attenuation is defined as the gradual loss of virulence of a pathogen.

Novobiocin-resistant strains of bacteria, such as, for example, *Edwardsiella ictaluri*, and *Streptococcus iniae*, were created by multiple passages of isolates of virulent strains of the bacteria of interest. Serial passage of these isolates over increasing concentrations of novobiocin produces strains with an attenuated pathogenicity efficacious for the preparation of live vaccines. The attenuation achieved by the high-level serial passage in liquid culture on increasing concentrations of novobiocin virtually eliminates the pathogenicity of the bacterium toward aquatic animals. The starting concentration for novobiocin that allowed overnight growth was approximately 12.5 µg/ml for *Edwardsiella ictaluri*, and approximately 1 ng/ml for *Streptococcus iniae*. The starting concentration for novobiocin-like coumermycin that allowed overnight growth was approximately 312.5 ng/ml for *Edwardsiella tarda*, and approximately 1 ng/ml for *Streptococcus agalactiae*.

A method for making live attenuated bacterial vaccines uses novobiocin or any chemical that functions the same as novobiocin, i.e. any DNA gyrase inhibitor also referred to as a novobiocin-like compound, such as, for example, coumermycin. Serial passages of bacteria isolates in increasing amounts of novobiocin in liquid culture produce novobiocin-resistant bacterial mutants. Determining the starting concentration of novobiocin or a novobiocin-like compound is microorganism dependent and determination of the concentration is well within the ordinary skill in the art given the detailed description and examples of the present specification. The bacteria are attenuated by serial passage in any suitable growth media, including, but not limited to, liquid media, solid media, or partial soft and partial liquid media. For example, *Edwardsiella ictaluri* and *Streptococcus iniae* were attenuated by serial passage in tryptic soy broth (TSB) containing increasing concentrations of novobiocin. *Streptococcus agalactiae* and *Edwardsiella tarda* were attenuated by serial passage in tryptic soy broth (TSB) containing increasing concentrations of coumermycin.

The *E. ictaluri* strains were passaged approximately 12 times using increasing concentrations of novobiocin. Initially *E. ictaluri* was able to grow overnight in brain heart infusion broth containing 12.5 µg/ml of novobiocin. Approximately 10 µl of that overnight culture was added into approximately 1 ml of tbrain heart infusion broth containing 25 µg/ml of novobiocin. If the cells were able to grow in brain heart infusion broth containing 25 µg/ml of novobiocin, approximately 10 µl of the overnight culture containing novobiocin at concentration of 25 µg/ml was then added into approximately 1 ml of brain heart infusion broth containing 50 µg/ml of novobiocin. However, if the cells from the overnight culture at concentration of 12.5 µg/ml of novobiocin were unable to grow in brain heart infusion broth containing 25 µg/ml of novobiocin, then approximately 10 µl of the overnight culture containing novobiocin at concentration of 12.5 µg/ml was added into approximately 1 ml of brain heart infusion broth containing novobiocin equal to or higher than 12.5 µg/ml but less than 25 µg/ml. This process was repeated multiple times until the cells were able to grow in culture media containing novobiocin at concentration of approximately 800 µg/ml.

The *S. iniae* strains were passed approximately 20 times using increasing concentrations of novobiocin, starting with a concentration of approximately 1 ng/ml which allowed overnight growth of *S. iniae*. Approximately 10 µl of that overnight culture was added into approximately 1 ml of tryptic soy broth containing 2 ng/ml of novobiocin. If the cells were able to grow in tryptic soy broth containing 2 ng/ml of novobiocin, approximately 10 µl of the overnight culture containing novobiocin at concentration of 2 ng/ml was then added into approximately 1 ml of tryptic soy broth containing 4 ng/ml of novobiocin. However, if the cells from the overnight culture at concentration of 1 ng/ml of novobiocin were unable to grow in tryptic soy broth containing 2 ng/ml of novobiocin, then approximately 10 µl of the overnight culture containing novobiocin at concentration of 1 ng/ml was added into approximately 1 ml of tryptic soy broth containing novobiocin equal to or higher than 1 ng/ml but less than 2 ng/ml. This process was repeated again and again until the cells were able to grow in culture media containing novobiocin at concentration of approximately 1000 ng/ml.

The *Streptococcus agalactiae* strains were passed approximately 20 times using increasing concentrations of coumermycin, a novobiocin-like antibiotic, starting with a concentration of approximately 1 ng/ml which allowed overnight growth of *S. agalactiae*. Approximately 10 µl of that overnight culture was added into approximately 1 ml of tryptic soy broth containing 2 ng/ml of coumermycin. If the cells were able to grow in tryptic soy broth containing 2 ng/ml of coumermycin, approximately 10 µl of the overnight culture containing coumermycin at concentration of 2 ng/ml was then added into approximately 1 ml of tryptic soy broth containing 4 ng/ml of coumermycin. However, if the cells from the overnight culture at concentration of 1 ng/ml of coumermycin were unable to grow in tryptic soy broth containing 2 ng/ml of coumermycin, then approximately 10 µl of the overnight culture containing coumermycin at concentration of 1 ng/ml was added into approximately 1 ml of tryptic soy broth containing coumermycin equal to or higher than 1 ng/ml but less than 2 ng/ml. This process was repeated again and again until the cells were able to grow in culture media containing coumermycin at concentration of approximately 5000 ng/ml.

The *Edwardsiella tarda* strains were passaged approximately 20 times using increasing concentrations of coumermycin, a novobiocin-like antibiotic, starting with a concentration of approximately 312.5 ng/ml which allowed overnight growth of *E. tarda*. Approximately 10 µl of that overnight culture was added into approximately 1 ml of tryptic soy broth containing 625 ng/ml of coumermycin. If the cells were able to grow in tryptic soy broth containing 625 ng/ml of coumermycin, approximately 10 µl of the overnight culture containing coumermycin at concentration of 625 ng/ml was then added into approximately 1 ml of tryptic soy broth containing 1250 ng/ml of coumermycin. However, if the cells from the overnight culture at concentration of 312.5 ng/ml of coumermycin were unable to grow in tryptic soy broth containing 625 ng/ml of coumermycin, then approximately 10 µl of the overnight culture containing coumermycin at concentration of 1 ng/ml was added into approximately 1 ml of tryptic soy broth containing coumermycin equal to or higher than 312.5 ng/ml but less than 625 ng/ml. This process was repeated again and again until the cells were able to grow in culture media containing coumermycin at concentration of approximately 640 µg/ml.

Another method to make antibiotic resistant attenuated vaccine strains includes using both rifampicin- and novobiocin-resistance strategy. Strains of bacteria such as, for example, *Aeromonas hydrophila*, were created by multiple passages of isolates of virulent strains of the bacteria of interest. Serial passage of these isolates over increasing concentrations of rifampicin and novobiocin produces strains with an attenuated pathogenicity efficacious for the preparation of live vaccines. The attenuation was achieved by serial passages in culture media containing increasing concentrations of novobiocin and rifampicin. The starting concentration of novobiocin and rifampicin that allowed overnight growth of *Aeromonas hydrophila* was approximately 10 µg/ml. Approximately 10 µl of that overnight culture was then added into approximately 1 ml of tryptic soy broth containing 20 µg/ml of novobiocin and 20 µg/ml of rifampicin. If the cells were able to grow in tryptic soy broth containing 20 µg/ml of novobiocin and rifampicin, approximately 10 µl of the overnight culture containing novobiocin and rifampicin at concentration of 20 µg/ml was then added into approximately 1 ml of tryptic soy broth containing 40 µg/ml of novobiocin and 40 µg/ml of rifampicin. However, if the cells from the overnight culture containing 10 µg/ml of novobiocin and 10 µg/ml of rifampicin were unable to grow in tryptic soy broth containing 20 µg/ml of novobiocin and 20 µg/ml of rifampicin, then approximately 10 µl of the overnight culture containing 10 µg/ml of novobiocin and 10 µg/ml of rifampicin was added into approximately 1 ml of tryptic soy broth containing novobiocin and rifampicin equal to or higher than 10 µg/ml but less than 20 µg/ml. This process was repeated multiple times until the cells were able to grow in culture media containing approximately 1600 µg/ml of novobiocin and 1600 µg/ml of rifampicin.

The native strain of *Aeromonas hydrophila* should be passaged a sufficient number of times such that in its new attenuated form it no longer possesses the ability of causing the disease state known as motile *Aeromonas* septicemia in tilapia, channel catfish, and other fish. The methodology for attenuation by serial passage is well know and documented in the art as exemplified by Schurig et al., (Vet. Micro. Volume 28, 171-188, 1991), herein incorporated by reference, who used rifampicin-resistant strategy and created modified live rifampicin-resistant *Brucella* vaccines.

Vaccination can be accomplishable by injection, oral ingestion, or by means of aqueous immersion. The bacterial agent is prepared for administration by formulation in an effective immunization dosage with an acceptable carrier or diluent, such as for example, water. Effective immunization dosage and immunologically effective amount or dosage are defined herein as being that amount which will induce complete or partial immunity or elicit a protective immune response in a treated fish against subsequent challenge by a virulent strain of a bacteria. Immunity is considered as having been induced in a population as evidenced by a decrease in the number of infected aquatic animals or a decrease in the severity of infection and is significantly higher than that of an unvaccinated control group measured at a confidence level of at least about 80% preferably measured at a confidence level of at least about 95%. The appropriate effective dosage can be readily determined by the practioner skilled in the art especially in light of the teachings of the present specification. One measure of protection following experimental challenge is relative percent survival (RPS) as described by Amend (Dev. Bio. Stand., Volume 49, 447-454, 1981) herein incorporated by reference. RPS is calculated according to the formula:

$$RPS = 1 - \frac{\% \text{ vaccinate mortality}}{\% \text{ control mortality}} \times 100$$

A positive vaccine effect is indicated by a RPS equal to or greater than about 60%. Typically, the vaccine is administered to an aquatic animal by bath immersion, intraperitoneal or intramuscular injection, and/or any oral delivery or immersion device. Aquatic animals are vaccinated by immersion in water containing approximately $1 \times 10^2$ to approximately $1 \times 10^9$ CFU/ml of immersion medium. Useable vaccination times are seen to range from about 1 minute to 120 minutes, depending on the penetration of the pathogen and the formulation of the vaccine. Temperature of the inoculation media may range within the physiologically acceptable limits of the aquatic animal involved, for tilapia and channel catfish preferably from about 18 degrees C. to about 32 degrees C., most preferably from about 20 degrees C. to about 30 degrees C. Concentrations of fish treated in the inoculation medium typically range from about 50 to about 100 fish/L, but, in the alternative may be determined on a weight basis and range from about 0.5 to about 2.5 kg/L. For intraperitoneal injection (IP injection), fish may be vaccinated within a range of about $1 \times 10^2$ CFU/fish to about $1 \times 10^9$ CFU/fish. The vaccine can be effectively administered any time after the fish attains immunocompetence, which for tilapia is at about two to fourteen days post-hatch and for channel catfish, after about 7-10 days post-hatch. Other species of fish can be immunized after about 21-30 days post-hatch or when they become immunocompetent to modified live vaccine administered by immersion.

To produce large amounts of the vaccine strains of bacteria for the preparation of vaccines, the bacterium may be cultivated under any conventional conditions and on media which promote growth of the bacterium.

Without being limited thereto, attenuated live *Edwardsiella ictaluri*, *Streptococcus iniae*, *Streptococcus agalactiae*, *Edwardsiella tarda* and *Aeromonas hydrophila* strains, for vaccine production, may be grown on a variety of liquid media types, including but not limited to, tryptic soy broth, brain heart infusion broth, and Lysogeny broth medium. The cultures are typically incubated at approximately 25-30 degrees C. for a period of time sufficient to produce maximum levels of cells, generally about 24 to 48 hours. Alternatively, the strains may be grown on a variety of sold media, including, but not limited to, Lysogeny broth agar, Helellea agar or tryptic soy agar (TSA). Without being limited thereto, conventional tryptic soy broth (TSB) is preferred. The production of the vaccine in this manner may be conducted by stationary culture of the strains at about 25-30 degrees C. for about 5 to about 7 days. All-vegetable based fermentation media are also preferred for use herein, as the use thereof eliminates the risks of the presence of animal products and infectious agents in the final vaccine product.

Live cells of the strains are prepared for administration to aquatic animals, especially fish, by formulation in an immunologically effective amount or dosage. The dose may further include pharmaceutically acceptable carriers and adjuvants know in the art.

As noted above, the cells may be formulated in an optional, pharmaceutically acceptable carrier such as water, physiological saline, mineral oil, vegetable oils, aqueous sodium carboxymethyl cellulose, or aqueous polyvinylpyrrolidone. The vaccine formulations may also contain optional adjuvants, antibacterial agents, or other pharmaceutically active agents as are conventional in the art. Without being limited thereto, suitable adjuvants include but are not limited to mineral oil, vegetable oils, alum, and Freund's incomplete adjuvant. Still other preferred adjuvants include microparticles or beads of biocompatible matrix materials. The microparticles may be composed of any biocompatible matrix as are conventional in the art, including but not limited to agar and polyacrylate. The practitioner skilled in the art will recognize that other carriers or adjuvants may be used as well. For example, other adjuvants which may be used are described by Webb and Winkelstein (In: Basic & Clinical Immunology, 1984, Stites et al, (Eds), Fifth edition, Lange Medical Publications, Los Altos, Calif., Pages 282-285, 1984), the contents of which are herein incorporated by reference.

The vaccines of the present invention may be administered to the subject animal by any convenient route which enables the cells to elicit an immune response, such as by IP or intramuscular injection, bath immersion, oral administration, or nasal administration. However, IP injection or bath immersion is preferred for primary immunization, while oral immunization is preferred for secondary or booster immunization, when necessary. It is also envisioned that the surface of the fish may be punctured such as described by Nakanishi et al. (Vaccine, Volume 20, 3764-3769, 2002) or otherwise abraded or slightly descaled, prior to or during bath immersion, to facilitate exposure of the vaccine to the animal's immune system. The vaccine may be administered in a single dose or in a plurality of doses. Dependent upon rearing conditions, the vaccine may be administered in multiple doses, the timing of which may be readily determined by the skilled artisan.

Vaccination against bacterial infection by bath immersion immunization offers several advantages over other routes of immunization. Among these advantages are lower cost per fish immunized, mass immunization of large numbers of fish, reduced stress, significantly higher rates of fish survival and the absence of adverse reactions to vaccination. Furthermore, bath immersion vaccination is an effective method for mass vaccination of smaller fish that cannot be injected or subjected to skin punctures. Alternatively, IP injection of commercially available fish vaccines is commonly employed on fresh or marine aquaculture farms due to their reliability and high efficacy despite high cost per fish immunized and stress to the fish.

The following examples are intended only to further illustrate the invention and are not intended to limit the scope of the invention as defined by the claims.

Example 1

A virulent strain of *Edwardsiella ictaluri*, strain AL93-58, was used for induction of novobiocin resistance. The strain was isolated in 1993 from diseased catfish in Alabama and is stored at the Aquatic Animal Health Research Unit, Auburn, Ala. Initial cultures of the AL93-58 strain were grown in brain heart infusion broth containing no antibiotics at approximately 27 degrees C. for about 24 hours. The virulent strain of AL93-58 was then subjected to selection for resistance to novobiocin By culturing the bacterium in brain heart infusion broth (BHI) (Fisher Scientific, Pittsburgh, Pa.) containing different concentrations of novobiocin as detailed in Table 1. The initial concentration of novobiocin that allowed growth of AL93-58 was approximately 12.5 µg/ml. After 12 passages of AL93-58 in BHI culture media containing higher doses of novobiocin, the novel novobiocin-resistant strain of AL93-58 Novo-800 (NRRL B-50348) was able to grow in BHI broth containing approximately 800 µg/ml of novobiocin.

Table 1 shows the novobiocin concentration and passage number used in the induction of novobiocin-resistant *E. ictaluri*. The starting concentration that allowed growth of AL93-58 was approximately 12.5 µg/ml. After 12 passages, the novel strain B-50348 of AL93-58 was able to grow in BHI containing approximately 800 µg/ml of novobiocin whereas the parent strain AL93-58 failed to grow in BHI containing 25 µg/ml or higher.

TABLE 1

Concentrations and passages used in the induction of novobiocin-resistant *E. ictaluri* strain from strain AL-93-58.

| Date | Passage No. | Novobiocin Conc µg/ml | Growth |
| --- | --- | --- | --- |
| Jun. 10, 2009 | 1 | 0 | Yes |
| Jun. 10, 2009 | 1 | 12.5 | Yes |
| Jun. 10, 2009 | 1 | 25 | No |
| Jun. 11, 2009 | 2 | 0 | Yes |
| Jun. 11, 2009 | 2 | 12.5 | Yes |
| Jun. 11, 2009 | 2 | 25 | No |
| Jun. 12, 2009 | 3 | 0 | Yes |
| Jun. 12, 2009 | 3 | 12.5 | Yes |
| Jun. 12, 2009 | 3 | 25 | No |
| Jun. 15, 2009 | 4 | 0 | Yes |
| Jun. 15, 2009 | 4 | 12.5 | Yes |
| Jun. 15, 2009 | 4 | 15 | Yes |
| Jun. 15, 2009 | 4 | 20 | Yes |
| Jun. 16, 2009 | 5 | 0 | Yes |
| Jun. 16, 2009 | 5 | 20 | Yes |
| Jun. 16, 2009 | 5 | 25 | Yes |
| Jun. 16, 2009 | 5 | 30 | Yes |
| Jun. 16, 2009 | 5 | 50 | Yes |
| Jun. 16, 2009 | 5 | 75 | Yes |
| Jun. 16, 2009 | 5 | 100 | Yes |
| Jun. 17, 2009 | 6 | 0 | Yes |
| Jun. 17, 2009 | 6 | 100 | Yes |
| Jun. 17, 2009 | 6 | 150 | Yes |
| Jun. 17, 2009 | 6 | 200 | Yes |
| Jun. 18, 2009 | 7 | 0 | Yes |
| Jun. 18, 2009 | 7 | 200 | Yes |

TABLE 1-continued

Concentrations and passages used in the induction of novobiocin-resistant *E. ictaluri* strain from strain AL-93-58.

| Date | Passage No. | Novobiocin Conc µg/ml | Growth |
|---|---|---|---|
| Jun. 18, 2009 | 7 | 250 | Yes |
| Jun. 18, 2009 | 7 | 300 | Yes |
| Jun. 19, 2009 | 8 | 0 | Yes |
| Jun. 19, 2009 | 8 | 300 | Yes |
| Jun. 19, 2009 | 8 | 350 | No |
| Jun. 19, 2009 | 8 | 400 | No |
| Jun. 20, 2009 | 9 | 0 | Yes |
| Jun. 20, 2009 | 9 | 300 | Yes |
| Jun. 20, 2009 | 9 | 350 | Yes |
| Jun. 20, 2009 | 9 | 400 | Yes |
| Jun. 23, 2009 | 10 | 0 | Yes |
| Jun. 23, 2009 | 10 | 400 | Yes |
| Jun. 23, 2009 | 10 | 450 | Yes |
| Jun. 23, 2009 | 10 | 500 | Yes |
| Jun. 24, 2009 | 11 | 0 | Yes |
| Jun. 24, 2009 | 11 | 500 | Yes |
| Jun. 24, 2009 | 11 | 550 | Yes |
| Jun. 24, 2009 | 11 | 600 | Yes |
| Jun. 25, 2009 | 12 | 0 | Yes |
| Jun. 25, 2009 | 12 | 600 | Yes |
| Jun. 25, 2009 | 12 | 650 | Yes |
| Jun. 25, 2009 | 12 | 700 | Yes |
| Jun. 25, 2009 | 12 | 750 | Yes |
| Jun. 25, 2009 | 12 | 800 | Yes |

Example 2

The growth and biochemical characteristics of *Edwardsiella ictaluri* Novo-800 were determined and compared to other strains of *E. ictaluri*. When *Edwardsiella ictaluri* AL93-58, *Edwardsiella ictaluri* Novo-800, and a rifampicin resistant *Edwardsiella ictaluri* RE-33 as described by Klesius and Shoemaker (1999, Adv. Vet. Med., Volume 41, 523-537) were plated on 5% sheep blood agar plates, the growth of *Edwardsiella ictaluri* AL93-58 were the fastest, followed by *Edwardsiella ictaluri* RE-33. However, the growth of *Edwardsiella ictaluri* Novo-800 was the slowest (FIG. 1).

Biochemical analysis using API-20E bacterial identification test strip (Biomérieux, Durham, N.C.) revealed that *Edwardsiella ictaluri* AL93-58, *Edwardsiella ictaluri* Novo-800, and *Edwardsiella ictaluri* RE-33 were identical (Table 2).

TABLE 2

Results of the API-20E bacterial identification test strip for *Edwardsiella ictaluri* AL93-58, *Edwardsiella ictaluri* Novo-800, and *Edwardsiella ictaluri* RE-33

| Tests | Reactions/Enzymes | AL93-58 | Novo-800 | RE-33 |
|---|---|---|---|---|
| ONPG | β-galactosidase | negative | negative | negative |
| ADH | Arginine dihydrolase | negative | negative | negative |
| LDC | Lysine decarboxylase | positive | positive | positive |
| ODC | Ornithine decarboxylase | negative | negative | negative |
| CIT | Citrate utilization | negative | negative | negative |
| $H_2S$ | $H_2S$ production | negative | negative | negative |
| URE | Urease | negative | negative | negative |
| TDA | Tryptophane deaminase | positive | positive | positive |
| IND | Indole production | negative | negative | negative |
| VP | Acetoin production | positive | positive | positive |
| GEL | Gelatinase | negative | negative | negative |
| GLU | Fermentation/oxidation (glucose) | positive | positive | positive |
| MAN | Fermentation/oxidation (mannitol) | negative | negative | negative |
| INO | Fermentation/oxidation (inositol) | negative | negative | negative |
| SOR | Fermentation/oxidation (sorbitol) | negative | negative | negative |
| RHA | Fermentation/oxidation (rhamnose) | negative | negative | negative |
| SAC | Fermentation/oxidation (saccharose) | negative | negative | negative |
| MEL | Fermentation/oxidation (melibiose) | negative | negative | negative |
| AMY | Fermentation/oxidation (amygdalin) | negative | negative | negative |
| ARA | Fermentation/oxidation (arabinose) | negative | negative | negative |
|

Example 4

The safety of *Edwardsiella ictaluri* Novo-800 to catfish by intraperitoneal injection was compared to *Edwardsiella ictaluri* RE-33 and *Edwardsiella ictaluri* AL93-58. All three strains of *Edwardsiella ictaluri* were cultured overnight in brain heart infusion (BHI) broth at 27° C. All catfish (Industry pool strain, USDA, ARS, Catfish Genetics Research Unit, Stoneville, Miss.) used in this study were raised at the USDA ARS Aquatic Animal Health Research facility located at Auburn, Ala. and naïve to *Edwardsiella ictaluri*. Different concentrations (colony forming unit/CFU) of *Edwardsiella ictaluri* were injected to catfish intraperitoneally. Mortalities were recorded for 14 days post exposure to *E. ictaluri*.

When 11 g fish were injected with approximately $2.4 \times 10^6$ CFU of *Edwardsiella ictaluri* AL93-58, all fish died (Table 4). When same size fish were injected approximately $2.2 \times 10^6$ CFU of *Edwardsiella ictaluri* RE-33, mortality was about 75%. However, when same size fish were injected approximately $2.8 \times 10^6$ CFU of *Edwardsiella ictaluri* Novo-800, no fish died (Table 4).

When 14 g fish were intraperitoneally injected with approximately $2.5 \times 10^6$ CFU of *Edwardsiella ictaluri* AL93-58, about 95% fish died (Table 4). When same size fish were intraperitoneally injected with approximately $2.4 \times 10^6$ CFU of *Edwardsiella ictaluri* RE-33, mortality was about 65%. However, when same size fish were intraperitoneally injected with approximately $2.8 \times 10^6$ CFU or approximately $4.2 \times 10^6$ CFU of *Edwardsiella ictaluri* Novo-800, no fish died (Table 4).

TABLE 4

Safety of *Edwardsiella ictaluri* AL93-58, RE-33, and Novo-800 to catfish by intraperitoneal injection

| Strain used in injection | Fish weight (g) | No. of fish | Exposure method | Dose[a] | Mortality (%)[b] |
|---|---|---|---|---|---|
| BHI[c] control | 11 | 20 | injection | — | 0 |
| AL93-58 | 11 | 20 | injection | $2.4 \times 10^6$ | 100 |
| AL93-58 | 11 | 20 | injection | $1.6 \times 10^6$ | 95 |
| AL93-58 | 11 | 20 | injection | $1.2 \times 10^6$ | 80 |
| AL93-58 | 11 | 20 | injection | $9.6 \times 10^5$ | 70 |
| RE-33 | 11 | 20 | injection | $2.2 \times 10^6$ | 75 |
| RE-33 | 11 | 20 | injection | $1.5 \times 10^6$ | 60 |
| RE-33 | 11 | 20 | injection | $1.1 \times 10^6$ | 45 |
| RE-33 | 11 | 20 | injection | $8.9 \times 10^5$ | 35 |
| Novo-800 | 11 | 20 | injection | $2.8 \times 10^6$ | 0 |
| Novo-800 | 11 | 20 | injection | $1.8 \times 10^6$ | 0 |
| Novo-800 | 11 | 20 | injection | $1.4 \times 10^6$ | 0 |
| Novo-800 | 11 | 20 | injection | $1.1 \times 10^6$ | 0 |
| BHI control | 14 | 40 | injection | — | 0 |
| AL93-58 | 14 | 40 | injection | $2.5 \times 10^6$ | 95 |
| AL93-58 | 14 | 40 | injection | $1.7 \times 10^6$ | 93 |
| AL93-58 | 14 | 40 | injection | $1.3 \times 10^6$ | 93 |
| AL93-58 | 14 | 40 | injection | $1.0 \times 10^6$ | 88 |
| RE-33 | 14 | 40 | injection | $3.6 \times 10^6$ | 83 |
| RE-33 | 14 | 40 | injection | $2.4 \times 10^6$ | 65 |
| RE-33 | 14 | 40 | injection | $1.8 \times 10^6$ | 30 |
| RE-33 | 14 | 40 | injection | $1.4 \times 10^6$ | 33 |
| Novo-800 | 14 | 40 | injection | $4.2 \times 10^6$ | 0 |
| Novo-800 | 14 | 40 | injection | $2.8 \times 10^6$ | 0 |
| Novo-800 | 14 | 40 | injection | $2.1 \times 10^6$ | 0 |
| Novo-800 | 14 | 40 | injection | $1.7 \times 10^6$ | 0 |

[a] dose by injection is in the unit of CFU per fish; vaccination concentration by IM is in the unit of CFU per milliliter
[b] cumulative mortality was calculated at 14 days post treatment days post exposure
[c] brain heart infusion culture media

Example 5

Channel catfish, ranging in size from approximately 8 to 14 grams and age from approximately 3 months to 9 months, were used to test a vaccine containing *Edwardsiella ictaluri* strain Novo-800 (NRRL B-50348). Novo-800 was cultured in BHI broth at approximately 27 degrees C. at approximately 125 rpm overnight before vaccination. Catfish were vaccinated by IP injection. For sham-vaccination controls, channel catfish were IP injected with BHI. After one and two months post vaccination, channel catfish were challenged by virulent *Edwardsiella ictaluri* strain AL 93-58 strain of *E. ictaluri* through IP injection using a dose of approximately $1.8 \times 10^5$ CFU per fish which was the $LD_{50}$ value of AL93-58 by IP injection. Mortalities were recorded for approximately 14 days post challenge and the presence or absence of *E. icatluri* in dead fish were determined as described above. Results of experimental challenge were presented as relative percent survival (RPS) as described previously (Klesius et al., 2000, supra). RPS was calculated according to the following formula:

RPS={1−vaccinated mortality/control mortality}×100.

Figure 2:
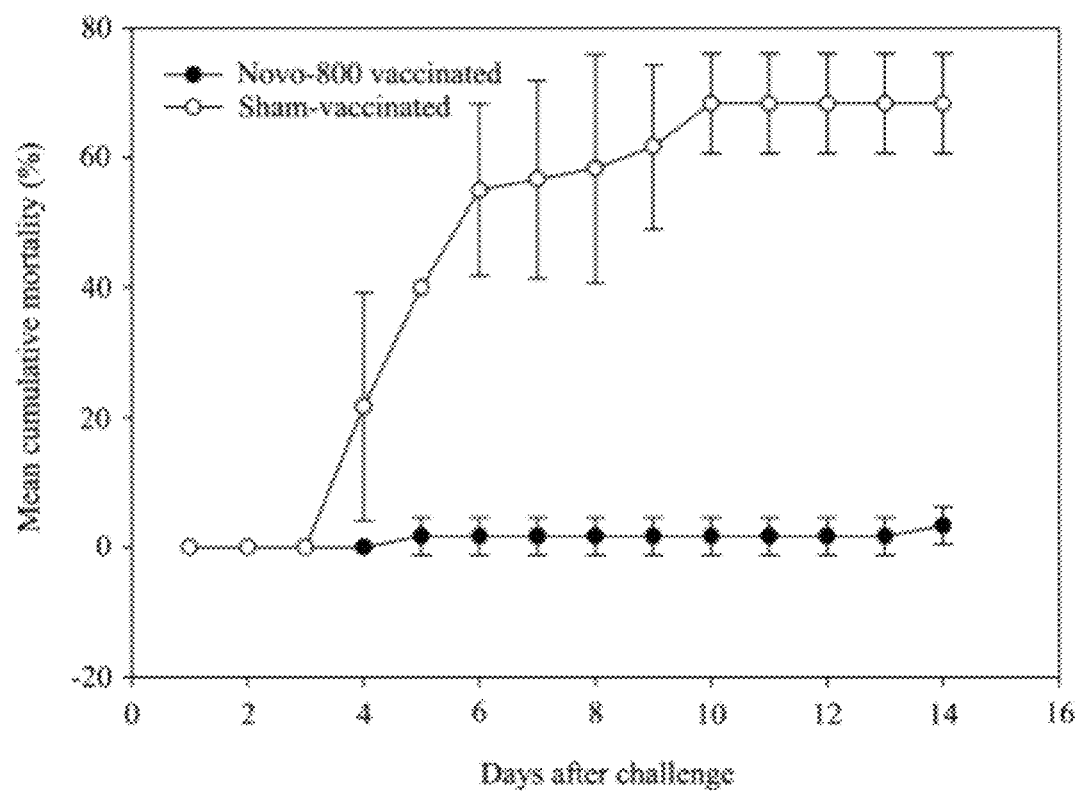
FIG. 2 is a graph showing daily mean percent cumulative mortality of intraperitoneal injected vaccinated channel catfish challenged by virulent AL93-58 strain of *Edwardsiella ictaluri* through intraperitoneal injection. Daily mean percent cumulative mortalities were calculated from three trials. Data are represented as mean±S.D. from the three trials.

At 22 days post vaccination, when *Edwardsiella ictaluri* Novo-800 vaccinated catfish were challenged by virulent *Edwardsiella ictaluri* AL93-58, only 5% fish died (Table 5). However, 70% fish died in the BHI sham vaccinated control. The RPS of *Edwardsiella ictaluri* Novo-800 vaccinated fish at 22 dpv was 93% (Table 5). At 32 days post vaccination, when Novo-800 vaccinated catfish were challenged by virulent *Edwardsiella ictaluri* AL93-58, only 5% fish died. However, 60% fish died in the BHI sham vaccinated control. The RPS of *Edwardsiella ictaluri* Novo-800 vaccinated fish at 32 dpv was 92% (Table 5). At 63 days post vaccination, when *Edwardsiella ictaluri* Novo-800 vaccinated catfish were challenged by virulent *Edwardsiella ictaluri* AL93-58, no fish died. However, 75% fish died in the BHI sham vaccinated control. The RPS of *Edwardsiella ictaluri* Novo-800 vaccinated fish at 63 dpv was 100% (Table 5). When catfish were challenged by virulent *Edwardsiella ictaluri* AL93-58, cumulative mortalities of *Edwardsiella ictaluri* Novo-800 vaccinated fish at different time points (different days post vaccination) were significantly ($P<0.05$) lower than that of BHI sham-vaccinated fish (FIG. 2).

TABLE 5

Cumulative mortality and relative percent survival (RPS) of intraperitoneal injection vaccinated catfish challenged with *Edwardsiella ictaluri* AL93-58 virulent strain

| Vaccine group | Vaccination dose (CFU/fish) | Fish starting weight (g) | Challenge Dose (CFU/fish) | dpv[a] | Mortality (%) | RPS[b] (%) |
|---|---|---|---|---|---|---|
| BHI[c] control | — | 11 | $1.7 \times 10^5$ | 22 | 70 | — |
| B-50348 | $1.84 \times 10^6$ | 11 | $1.7 \times 10^5$ | 22 | 5 | 93 |
| B-50348 | $1.38 \times 10^6$ | 11 | $1.7 \times 10^5$ | 22 | 5 | 93 |
| BHI control | — | 8 | $2.0 \times 10^5$ | 32 | 60 | — |
| B-50348 | $8.67 \times 10^6$ | 8 | $2.0 \times 10^5$ | 32 | 5 | 92 |
| BHI control | — | 8 | $2.2 \times 10^5$ | 63 | 75 | — |
| B-50348 | $8.67 \times 10^6$ | 8 | $2.2 \times 10^5$ | 63 | 0 | 100 |

[a] days post vaccination;
[b] relative percent survival;
[c] brain heart infusion broth

Example 6

The efficacy of *Edwardsiella ictaluri* Novo-800 through bath immersion vaccination was tested on channel catfish. Channel catfish used in this experiment were approximately 8 grams and approximately 3 months old. *Edwardsiella ictaluri*

Novo-800 was cultured in BHI broth at approximately 27° C. at about 125 rpm overnight before vaccination. Catfish were bath immersed in water containing approximately $2.7 \times 10^7$ CFU/ml of *Edwardsiella ictaluri* Novo-800 for about 1 h. As sham-vaccination controls, channel catfish were bath immersed in water containing same amount of BHI used for *Edwardsiella ictaluri* Novo-800 vaccine (sham vaccination). After about 37 and about 57 days post vaccination, channel catfish were challenged by virulent *Edwardsiella ictaluri* AL93-58 through intraperitoneal injection. Mortalities were recorded for about 14 days post challenge. Results of experimental challenge were presented as RPS.

When *Edwardsiella ictaluri* Novo-800 vaccinated catfish were challenged by virulent *Edwardsiella ictaluri* AL93-58, no fish died at about 37 days post vaccination. However, approximately 30% of the fish died in the BHI sham vaccinated control. The relative percent survival of *Edwardsiella ictaluri* Novo-800 vaccinated fish at about 37 dpv was 100% (Table 6).

At 57 days post vaccination, when *Edwardsiella ictaluri* Novo-800 vaccinated catfish were challenged by virulent *Edwardsiella ictaluri* AL93-58, no fish died. However, 40% fish died in the BHI sham vaccinated control. The RPS of *Edwardsiella ictaluri* Novo-800 vaccinated fish at 57 dpv was 100% (Table 6).

Figure 3:
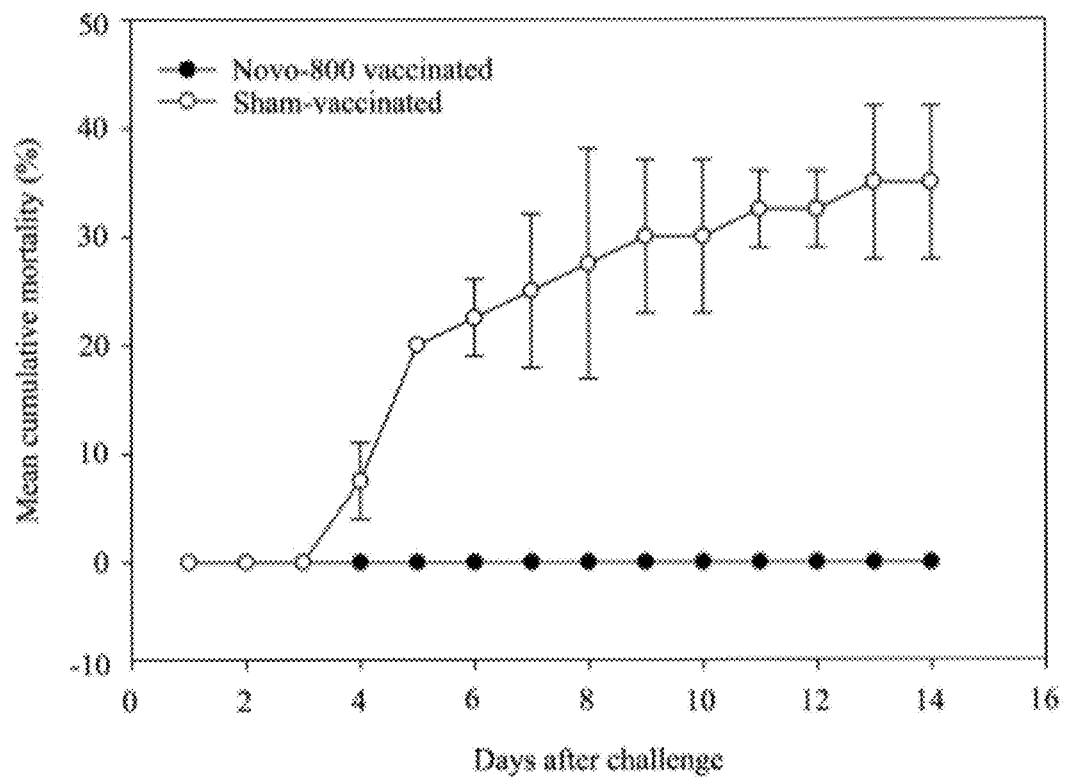
FIG. 3 is a graph showing daily mean percent cumulative mortality of immersion vaccinated channel catfish challenged by virulent AL93-58 strain of *Edwardsiella ictaluri* through intraperitoneal injection. Daily mean percent cumulative mortalities were calculated from two trials. Data are represented as mean±S.D. from the two trials.
Figure 4:
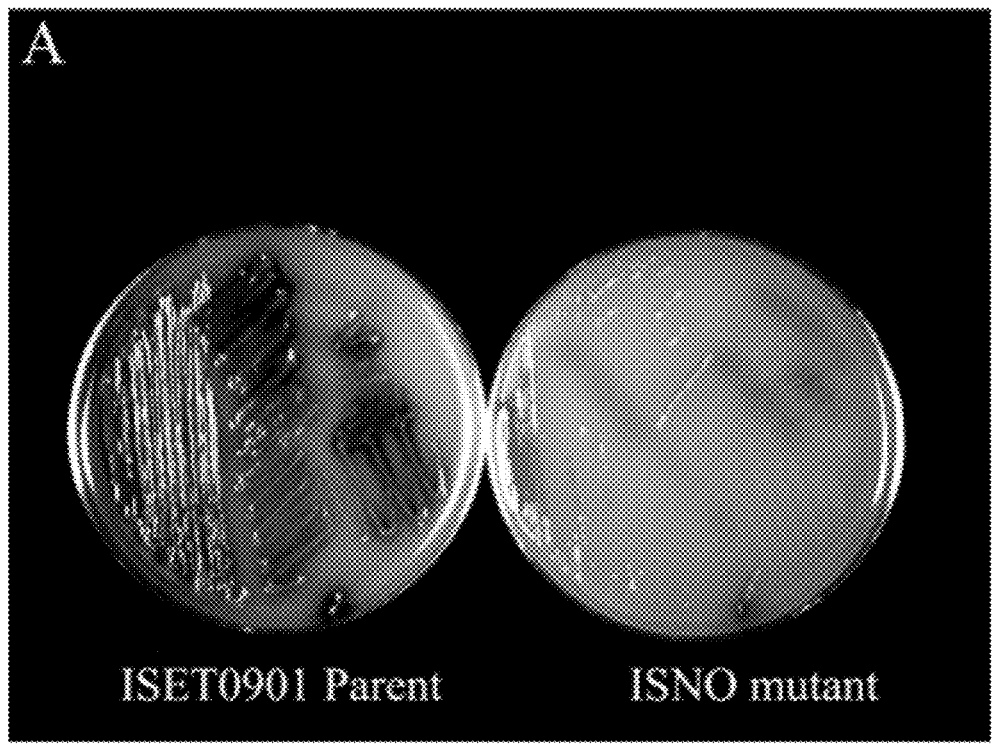
FIGS. 4A and 4B are photographs showing the growth of *Streptococcus iniae* ISET0901 and *Streptococcus iniae* ISNO on 5% sheep blood agar plates. The two strains were streaked out onto 5% sheep blood agar plates and incubated at 27° C. for approximately 24 h (FIG. 4A) or approximately 96 h (FIG. 4B). The dark area around the bacteria colony on 5% sheep blood agar plates represents hemolytic activity.
Figure 4:
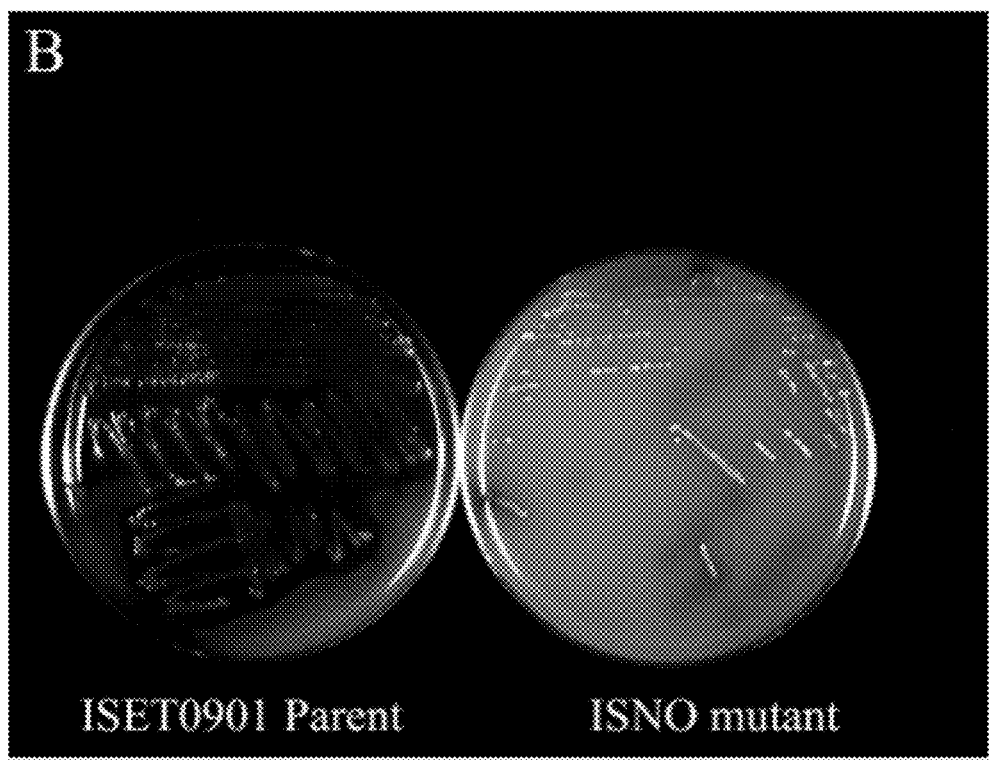

When catfish were challenged by virulent *Edwardsiella ictaluri* AL93-58, cumulative mortalities of *Edwardsiella ictaluri* Novo-800 vaccinated fish at different time points (different days post vaccination) were significantly ($P<0.05$) lower than that of BHI sham-vaccinated fish (FIG. 3).

TABLE 6

Cumulative mortality and relative percent survival (RPS) of vaccinated catfish challenged by virulent *Edwardsiella ictaluri* AL93-58

| Vaccine group | Fish starting weight (g) | Challenge Dose (CFU/fish) | No. fish challenged | dpv[a] | Mortality (%) | RPS[b] (%) |
|---|---|---|---|---|---|---|
| BHI[c] control | 8 | $1.2 \times 10^5$ | 20 | 37 | 30 | — |
| Novo-800 | 8 | $1.2 \times 10^5$ | 20 | 37 | 0 | 100 |
| BHI control | 8 | $2.2 \times 10^5$ | 20 | 57 | 40 | — |
| Novo-800 | 8 | $2.2 \times 10^5$ | 20 | 57 | 0 | 100 |

[a]vaccination concentration by immersion is in the unit of CFU per milliliter
[b]relative percent survival
[c]brain heart infusion culture media Example 7

Eight *Streptococcus iniae* isolates obtained from different fish species exhibiting clinical streptococcal disease and from different geographical regions (Table 7) were used for the induction of novobiocin resistance. The archived isolates were recovered from frozen stocks (approximately 2 ml aliquots stored at approximately −80 degrees C.) and grown in tryptic soy broth (TSB) (Fisher Scientific, Pittsburgh, Pa.) for approximately 24 hours at approximately 28 degrees C. All strains were cultured in tryptic soy broth containing different concentrations of novobiocin sodium salt (Promega, Madison, Wis.) for approximately 24 to 48 hours at approximately 28 degrees C. The initial concentration of novobiocin that allowed overnight growth of *Streptococcus iniae* was approximately 1 ng/ml. Approximately 10 µl of that overnight culture was added into approximately 1 ml of tryptic soy broth containing 2 ng/ml of novobiocin. If the cells were able to grow in tryptic soy broth containing 2 ng/ml of novobiocin, approximately 10 µl of the overnight culture containing novobiocin at concentration of 2 ng/ml was then added into approximately 1 ml of tryptic soy broth containing 4 ng/ml of novobiocin. However, if the cells from the overnight culture at concentration of 1 ng/ml of novobiocin were unable to grow in tryptic soy broth containing 2 ng/ml of novobiocin, then approximately 10 µl of the overnight culture containing novobiocin at concentration of 1 ng/ml was added into approximately 1 ml of tryptic soy broth containing novobiocin equal to or higher than 1 ng/ml but less than 2 ng/ml. This process was repeated again and again until the cells were able to grow in culture media containing novobiocin at concentration of approximately 1000 ng/ml. After about 20 passages of *Streptococcus iniae* in TSB culture media containing the same or higher concentrations of novobiocin, all eight *Streptococcus iniae* strains were able to grow in TSB containing approximately 1 µg/ml of novobiocin.

TABLE 7

*Streptococcus iniae* isolates used in this study

| Isolate designation | Location | Species of fish |
|---|---|---|
| IF6-F3 | Minnesota, USA | *Oreochromis niloticus* × *O. aureus* |
| ISET0901 | Israel | *Oreochromis niloticus* |
| Kent-02 | California, USA | *Morone saxatilis* × *M. chrysops* |
| Uruguay 1.1/28 | Uruguay | *Acipenser gueldenstaedtii* |
| 15-Br | Minnesota, USA | *Oreochromis niloticus* |
| Uruguay 1 | Uruguay | *Acipenser gueldenstaedtii* |
| Kent 08 | California, USA | *Morone saxatilis* × *M. chrysops* |
| 35-Br | Idaho, USA | *Oreochromis* spp. |

The eight parent and novobiocin-resistant *Streptococcus iniae* strains were then grown on approximately 5% sheep blood agar plates (Thermo Fisher Scientific Remel Products, Lenexa, Kans.) for bacterial identification. Bacteria isolates were identified by API 20 Strep test (BioMerieux, Durham, N.C.) and gas chromatography analysis of fatty acid methyl ester using MIDI microbial identification system (MIDI, Newark, Del.) according to established procedures (Shoemaker et al, 2005, J. Aqua Animal Health Volume 17, 267-274).

Biochemical analysis using API-20 strep identification test revealed that all isolates shared similar biochemical profiles to know *S. iniae* deposited in the Mini API strip reading system (BioMerieux, Durham, N.C.), which were positive for β-glucosidase, arginine dihydrolase, ribodse acidification, L-arabinose acidification, mannitol acidification, trehalose acidification, starch acidification, and glycogen acidification, but negative for all others. Gas chromatograph analysis of fatty acid methyl ester using MIDI microbial identification system also confirmed that parent and novobiocin-resistant mutants were *Streptococcus iniae*. When parent *Streptococcus iniae* ISET0901 isolate and novobiocin-resistant *S. iniae* ISNO were plated onto 5% sheep blood agar plates, parent isolate grew much faster than the novobiocin-resistant ISNO isolate, as shown in FIGS. 5A and 5B. Parent *S. iniae* ISET0901 isolate also showed hemolytic activity, whereas ISNO failed to show hemolytic activity (FIGS. 4A and 4B).

Example 8

To study the virulence of novobiocin-resistant *S. iniae* isolates compared to their parent isolates, all bacteria were cultured overnight in TSB at approximately 28 degrees C. An optical density (OD) of 1.0 of the bacterial cultures was measured at about 540 nm using Thermospectronic spectrophotomer (Fisher Scientific, Pittsburgh, Pa.). Serial dilutions (in triplicates) of each isolate were prepared in TSB and approximately 100 μl of serially diluted *S. iniae* were plated onto TSA plates. After about 24 hours incubation at approximately 28 degrees C., the average number of CFU/ml was calculated for all isolates. Similar amount of each parent and novobiocin-resistant isolate was exposed to Nile tilapia, having a mean weight of approximately 10.4±0.6 grams, through intraperitoneal (IP) injection. Three concentrations (CFU/ml) for each isolate were injected into Nile tilapia using ten fish per concentration. All fish used were male tilapia raised at the USDA ARS Aquatic Animal Health Research facility located at Auburn, Ala. Fish were acclimated in flow-through 57-L aquaria supplied with approximately 0.5 L h$^{-1}$ dechlorinated water for about 10 days prior to experiments. A 12:12 hour light:dark period was maintained and supplemental aeration was supplied by an air stone. Fish were fed approximately 3% body weight daily with commercial dry fish food. During the experiment, the mean dissolved oxygen was approximately 5.6 mg L$^{-1}$, temperature was approximately 26 degrees C., pH was approximately 7.1, and hardness was approximately 100 mg L$^{-1}$. Mortalities were recorded for approximately 14 days post exposure to *S. iniae*.

Virulence data of both novobiocin-reistant and susceptible parent isolates of *S. iniae* are shown in Table 8. When novobiocin-resistant *S. iniae* isolates were IP injected into Nile tilapia, four out of eight isolates (ISET0901-N, Kent02-N, Uruguay 1-N, and 35Br-N) caused no mortality or less than 10% mortality at all three injection doses. However, when injected at a high dose of 2×10$^7$ CFU per fish, their respective parent isolates caused 100, 50, 40 and 30% mortality, respectively (Table 8). The most virulent parent *Streptococcus iniae* isolates were *Streptococcus iniae* IF6-F3 and *Streptococcus iniae* ISET0901, both of which killed 100% of Nile tilapia at a dose of approximately 2×10$^7$ CFU per fish (Table 8).

TABLE 8

Virulence of novobiocin-resistant (N) and parent isolates (P) of *S. iniae* to Nile tilapia by intraperitoneal injection

| Isolate name | Mortality at 2 × 10$^7$ dose (%) | Mortality at 1 × 10$^7$ dose[b] (%) | Mortality at 1 × 10$^6$ dose (%) |
|---|---|---|---|
| IF6-F3-N[a] | 70 | 70 | 0 |
| IF6-F3-P[b] | 100 | 80 | 40 |
| ISET0901-N | 0 | 0 | 0 |
| ISET0901-P | 100 | 100 | 100 |
| Kent02-N | 0 | 10 | 0 |
| Kent02-P | 50 | 10 | 0 |

TABLE 8-continued

Virulence of novobiocin-resistant (N) and parent isolates (P) of *S. iniae* to Nile tilapia by intraperitoneal injection

| Isolate name | Mortality at 2 × 10$^7$ dose (%) | Mortality at 1 × 10$^7$ dose[b] (%) | Mortality at 1 × 10$^6$ dose (%) |
|---|---|---|---|
| Uruguay1.1-N | 10 | 10 | 10 |
| Uruguay1.1-P | 10 | 0 | 0 |
| 15Br-N | 50 | 50 | 40 |
| 15Br-P | 50 | 50 | 50 |
| Uruguay 1-N | 10 | 0 | 0 |
| Uruguay 1-P | 40 | 0 | 0 |
| Kent08-N | 20 | 0 | 0 |
| Kent08-P | 20 | 0 | 0 |
| 35Br-N | 0 | 0 | 0 |
| 35Br-P | 30 | 10 | 0 |

[a]N stands for novobiocin-resistant isolate;
[b]P stands for parent isolate.

Example 9

Nile tilapia were vaccinated with novobiocin-resistant *Streptococcus iniae* isolates and then challenged with parent isolates to test for protection against *Streptococcus iniae*. Attenuated novobiocin-resistant *S. iniae* vaccines were cultured in TSB at approximately 28 degrees C. at approximately 125 rpm overnight before vaccination. Fish were vaccinated by IP injection. Initial screen for the most safe and effective *S. iniae* vaccine were performed by using three vaccination doses in a total volume of approximately 100 μl for each vaccine and ten fish per dose. As sham vaccination controls, approximately 100 μl of TSB were injected into each fish, 10 fish total.

At approximately thirty days post vaccination (dpv), fish were challenged by the parent isolate of *S. iniae* through IP injection. Mortalities were recorded for approximately 14 days post challenge. Results of *S. iniae* challenge are presented as relative percent survival (RPS) and RPS was calculated as described above in example 5. The four novobiocin-resistant *S. iniae* isolates that killed less than about 10% tilapia when injected at high dose were then subjected to initial vaccine screen. When novobiocin-resistant ISET0901 (ISET0901-Novo, called ISNO, NRRL B-50368) vaccinated fish were challenged by its virulent parent isolate at 28 dpv, relative percent survival of vaccinated fish was 100% (Table 9). However, when novobiocin-resistant Uruguay 1 vaccinated fish were challenged by its virulent parent isolate, RPS value at 28 dvp was only about 33% (Table 8). Novobiocin-resistant 35Br and Kent02 failed to protect fish at 28 dpv, with RPS value of zero (Table 9).

TABLE 9

Cumulative mortality and relative percent survival (RPS) of vaccinated tilapia challenged with virulent parent isolates

| Vaccine group | Vaccination dose (CFU/fish) | Isolate used for challenge | Challenge Dose (CFU/fish) | d.p.v.[a] | Mortality (%) | RPS[e] (%) |
|---|---|---|---|---|---|---|
| Sham TSB | — | ISET0901-P[d] | 1.0 × 10$^5$ | 28 | 90 | — |
| ISET0901-N[c] | 1.0 × 10$^7$ | ISET0901-P | 1.0 × 10$^5$ | 28 | 0 | 100 |
| Sham TSB | — | Uruguay1-P | 2.6 × 10$^8$ | 28 | 30 | — |
| Uruguay1-N | 1.3 × 10$^8$ | Uruguay1-P | 2.6 × 10$^8$ | 28 | 20 | 33 |
| Sham TSB | — | 35Br—P | 4.2 × 10$^7$ | 28 | 20 | — |

TABLE 9-continued

Cumulative mortality and relative percent survival (RPS) of vaccinated tilapia challenged with virulent parent isolates

| Vaccine group | Vaccination dose (CFU/fish) | Isolate used for challenge | Challenge Dose (CFU/fish) | d.p.v.[a] | Mortality (%) | RPS[e] (%) |
|---|---|---|---|---|---|---|
| 35Br—N | $2.1 \times 10^7$ | 35Br—P | $4.2 \times 10^7$ | 28 | 30 | 0 |
| Sham TSB | — | Kent02-P | $1.7 \times 10^8$ | 28 | 50 | — |
| Kent02-N | $8.5 \times 10^7$ | Kent02-P | $1.7 \times 10^8$ | 28 | 50 | 0 |

[a] days post vaccination;
[b] intraperitoneal injection;
[c] novobiocin-resistant isolate;
[d] virulent parent isolate;
[e] relative percent survival Example 10

To determine the effective immunization dose of *Streptococcus iniae* ISNO in Nile tilapia by intraperitoneal injection vaccination, six doses of approximately $1 \times 10^2$, $1 \times 10^3$, $1 \times 10^4$, $1 \times 10^5$, $1 \times 10^6$, and $1 \times 10^7$ CFU/fish in a total volume of approximately 1000 were intraperitoneally injected into Nile tilapia using 30 fish per dose. As sham-vaccination control, fish were injected in the same manner with TSB. All bacteria were cultured in TSB broth at approximately 28 degrees centigrade at about 125 rpm overnight before vaccination or challenge. At 28 days post vaccination, vaccinated fish were challenged by virulent parent strain *S. iniae* ISET0901 and the challenge dose was approximately $1.5 \times 10^7$ CFU per fish by injection.

To determine the effective immunization dose of *Streptococcus iniae* ISNO by immersion, concentrations of approximately $1 \times 10^5$, $1 \times 10^6$, and $1 \times 10^7$ CFU/ml in total volume of approximately 5 L were used. A total of 30 Nile tilapia per concentration were immersed for 4 hours in the presence of approximately 0.02% Tween-20. As sham-vaccination control, fish were bath immersed in TSB containing approximately 0.02% Tween-20.

Results of minimum vaccination dose of ISNO to protect tilapia from infection by virulent *S. iniae* ISET0901 are summarized in Table 10. When IP vaccinated fish were challenged by ISET0901 isolate at about 28 days post vaccination, RPS values were all 100% when vaccination dose was approximately $1 \times 10^4$ CFU/fish or higher (Table 10). When Nile tilapia were vaccinated at dose of approximately $1 \times 10^3$ CFU/fish by IP, RPS value of vaccinate fish was approximately 95%. Relative percent survival of IP vaccinated fish at the lowest vaccination dose of approximately $1 \times 10^2$ CFU/fish was approximately 86% (Table 10 and FIG. 6). When Nile tilapia was vaccinated by ISNO through bath immersion, RPS of vaccinated fish at about 28 days post vaccination was approximately 88% with the highest vaccination dose of approximately $1 \times 10^7$ CFU/ml. When the vaccination dose was reduced to approximately $1 \times 10^6$ CFU/ml, RSP value for vaccinated fish dropped to approximately 63% (Table 10) and when vaccination dose was decreased to approximately $1 \times 10^5$ CFU/ml, RPS value for vaccinated fish at about 28 days post vaccination was only approximately 13% (Table 10).

TABLE 10

Minimum effective vaccination dose of ISNO to protect tilapia from infection by virulent *S. iniae* ISET0901

| Vaccine group | Vaccination route | Vaccination dose[a] | Challenge Dose (CFU/fish) | d.p.v.[b] | Mortality (%) | RPS[e] (%) |
|---|---|---|---|---|---|---|
| Sham TSB | IP[c] | — | $1.0 \times 10^5$ | 28 | 84 | — |
| ISNO | IP | $1.0 \times 10^7$ | $1.0 \times 10^5$ | 28 | 0 | 100 |
| ISNO | IP | $1.0 \times 10^6$ | $1.0 \times 10^5$ | 28 | 0 | 100 |
| ISNO | IP | $1.0 \times 10^5$ | $1.0 \times 10^5$ | 28 | 0 | 100 |
| ISNO | IP | $1.0 \times 10^4$ | $1.0 \times 10^5$ | 28 | 0 | 100 |
| ISNO | IP | $1.0 \times 10^3$ | $1.0 \times 10^5$ | 28 | 4 | 95 |
| ISNO | IP | $1.0 \times 10^2$ | $1.0 \times 10^5$ | 28 | 12 | 86 |
| Sham TSB | IM[d] | — | $1.0 \times 10^5$ | 28 | 64 | — |
| ISNO | IM | $1.0 \times 10^7$ | $1.0 \times 10^5$ | 28 | 8 | 88 |
| ISNO | IM | $1.0 \times 10^6$ | $1.0 \times 10^5$ | 28 | 24 | 63 |
| ISNO | IM | $1.0 \times 10^5$ | $1.0 \times 10^5$ | 28 | 56 | 13 |

[a] vaccination dose for IP and IM was in the unit of CFU/fish and CFU/ml, respectively
[b] days post vaccination
[c] intraperitoneal injection
[d] bath immersion
[e] relative percent survival Example 11

The attenuated *S. iniae* (ISNO) obtained from ISET0901 isolate that showed best protection in the initial vaccine trial was then subjected to backpassage safety studies. One hundred and eighty fish were divided into two groups, control group and vaccine group, with 90 fish per group. The 90 fish were then divided into 6 fish tanks with 15 fish per tank.

Approximately one hundred microliters (μl) of *S. iniae* ISNO overnight bacterial culture containing approximately 1.0 to $1.5 \times 10^7$ CFU were IP injected into each tilapia. This dose was approximately 1000 times of the effective immunization dose (approximately $1.0 \times 10^4$ CFU of *Streptococcus iniae* ISNO). Control group fish were injected with TSB. About forty-eight hours later, five fish were taken from the first tank and homogenized. Approximately 100 μl of the homogenate was injected into each fish in Tank 2. The homogenate was also cultured on a blood agar plate to determine the presence or absence of *S. iniae*. This backpassage procedure was repeated five times using the rest of the fish. Mortality or adverse behavior or signs of disease were recorded for about 21 days post injection.

Of all fish exposed to *S. iniae* ISNO vaccine through IP injection, no mortality or signs of disease or adverse behavior was observed. No fish died in the back passage studies either after exposure to *S. iniae* ISNO. No *S. iniae* was isolated from fish exposed to *S. iniae* ISNO by IP in the first IP or the following backpassage through injection of homogenates.

Example 12

To test the efficacy of Streptococcus iniae ISNO against homologous Streptococcus iniae challenge, both Streptococcus iniae ISET0901 and Streptococcus iniae ISNO were cultured in TSB at about 28° C. at about 125 rpm overnight before vaccination or challenge. Vaccination of Streptococcus iniae ISNO was performed at vaccination dose of approximately $1.0 \times 10^7$ CFU in a total volume of approximately 0.1 ml per fish through intraperitoneal injection. Sham vaccination was performed by injecting approximately 0.1 ml of tryptic soy broth to each fish. At about 14, 28, 60, 90, and 180 dpv, ten fish from each vaccination group (sham- or Streptococcus iniae ISNO-vaccinated) at each time point were challenged by its parent isolate Streptococcus iniae ISET0901 (homologous isolate) at dose of approximately $1.0 \times 10^5$ CFU per fish through intraperitoneal injection. Mortalities were recorded for about 14 days post challenge. Results of Streptococcus iniae challenge were presented as RPS.

Figure 5:
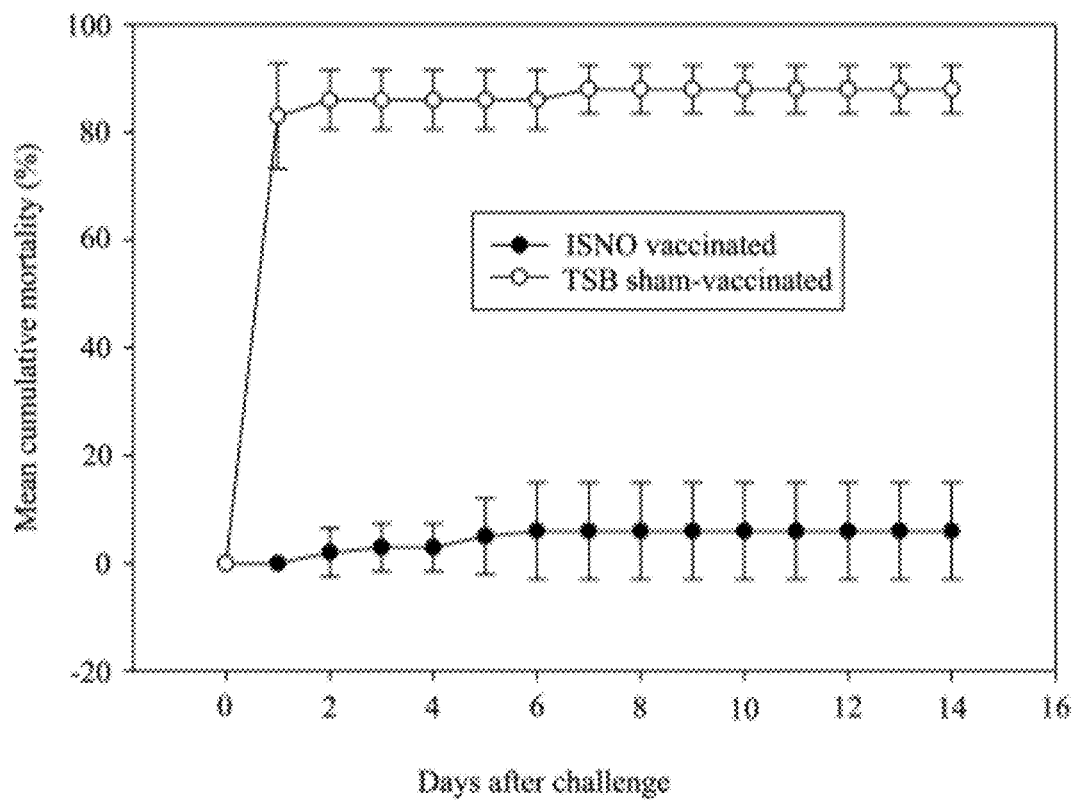
FIG. 5 is a graph showing daily mean percent cumulative mortality of Nile tilapia vaccinated through intraperitoneal injection with or without *Streptococcus iniae* ISNO and challenged with homologous virulent *Streptococcus iniae* ISET0901 strain through intraperitoneal injection. Daily mean percent cumulative mortalities were calculated from all vaccine trials at 14, 28, 60, 90, and 180 days post vaccination. Data are represented as mean±S.D. from all five trials.

At about 14 dpv, when TSB sham-vaccinated fish were challenged by virulent strain Streptococcus iniae ISET0901, approximately 90% fish died (Table 11). However, when Streptococcus iniae ISNO vaccinated fish were challenged by its homologous virulent strain Streptococcus iniae ISET0901, no fish died (Table 11). The RPS of Streptococcus iniae ISNO-vaccinated fish at about 14 dpv was 100% (Table 11). At about 28 dpv, when TSB sham-vaccinated fish were challenged by virulent strain Streptococcus iniae ISET0901, approximately 90% of the fish died (Table 11). However, when Streptococcus iniae ISNO vaccinated fish were challenged by its homologous virulent strain Streptococcus iniae ISET0901, no fish died (Table 11). The RPS of vaccinated fish at about 28 dpv was 100% (Table 11). At about 60 dpv, when TSB sham-vaccinated fish were challenged by virulent strain Streptococcus iniae ISET0901, approximately 90% of the fish died (Table 11). However, when Streptococcus iniae ISNO vaccinated fish were challenged by its homologous virulent strain Streptococcus iniae ISET0901, no fish died (Table 11). The RPS of vaccinated fish at about 60 dpv was 100% (Table 11). At about 90 dpv, when TSB sham-vaccinated fish were challenged by virulent strain Streptococcus iniae ISET0901, approximately 90% of the fish died (Table 11). However, when Streptococcus iniae ISNO vaccinated fish were challenged by its homologous virulent strain Streptococcus iniae ISET0901, only 10% fish died (Table 11). The RPS of vaccinated fish at about 90 dpv was approximately 89% (Table 11). At about 180 dpv, when TSB sham-vaccinated fish were challenged by virulent strain Streptococcus iniae ISET0901, approximately 90% of the fish died (Table 11). However, when Streptococcus iniae ISNO vaccinated fish were challenged by its homologous virulent strain Streptococcus iniae ISET0901, approximately 20% of the fish died (Table 11). The RPS of vaccinated fish at about 180 dpv was approximately 75% (Table 11). When fish were challenged by homologous Streptococcus iniae ISET0901, cumulative mortalities of Streptococcus iniae ISNO vaccinated fish at different time points were significantly (P<0.05) lower that of TSB sham-vaccinated fish (FIG. 5).

TABLE 11

Cumulative mortality and relative percent survival (RPS) of vaccinated Nile tilapia challenged with Streptococcus iniae ISET0901

| Vaccine group | Vaccination dose (CFU/fish) | Challenge Dose (CFU/fish) | dpv[a] | Mortality (%) | RPS[c] (%) |
|---|---|---|---|---|---|
| Sham TSB | — | $1.0 \times 10^5$ | 14 | 90 | — |
| ISNO | $1.0 \times 10^7$ | $1.0 \times 10^5$ | 14 | 0 | 100 |
| Sham TSB | — | $1.0 \times 10^5$ | 28 | 90 | — |
| ISNO | $1.0 \times 10^7$ | $1.0 \times 10^5$ | 28 | 0 | 100 |
| Sham TSB | — | $1.0 \times 10^5$ | 60 | 90 | — |
| ISNO | $1.0 \times 10^7$ | $1.0 \times 10^5$ | 60 | 0 | 100 |
| Sham TSB | — | $1.0 \times 10^5$ | 90 | 90 | — |
| ISNO | $1.0 \times 10^7$ | $1.0 \times 10^5$ | 90 | 10 | 89 |
| Sham TSB | — | $1.0 \times 10^5$ | 180 | 80 | — |
| ISNO | $1.0 \times 10^7$ | $1.0 \times 10^5$ | 180 | 20 | 75 |

[a]days post vaccination;
[b]intraperitoneal injection;
[c]relative percent survival

Example 13

To test the efficacy of Streptococcus iniae ISNO against heterologous Streptococcus iniae challenge, Streptococcus iniae bacteria were cultured in TSB at Approximately 28° C. at about 125 rpm overnight before vaccination or challenge. Vaccination of Streptococcus iniae ISNO was performed at vaccination dose of approximately $1.0 \times 10^7$ CFU per fish through intraperitoneal injection. Cross protection against heterologous Streptococcus iniae isolates were performed at about 60 days post vaccination. For cross protection experiments, five virulent heterologous isolates (Table 12) were used.

TABLE 12

Streptococcus iniae isolates used in the heterologous challenge study

| Isolate designation | Year isolated | Location | Species of fish |
|---|---|---|---|
| ARS-60 | 2004 | California, USA | Morone saxatilis × M. chrysops |
| IF6-F3 | 2008 | Minnesota, USA | Oreochromis niloticus |
| M10032405#F1K | 2010 | Maine, USA | Lates calcarifer |
| M10021102#F1K | 2010 | Maine, USA | Lates calcarifer |
| M10021101#F3CB | 2010 | Maine, USA | Lates calcarifer |

Figure 6:
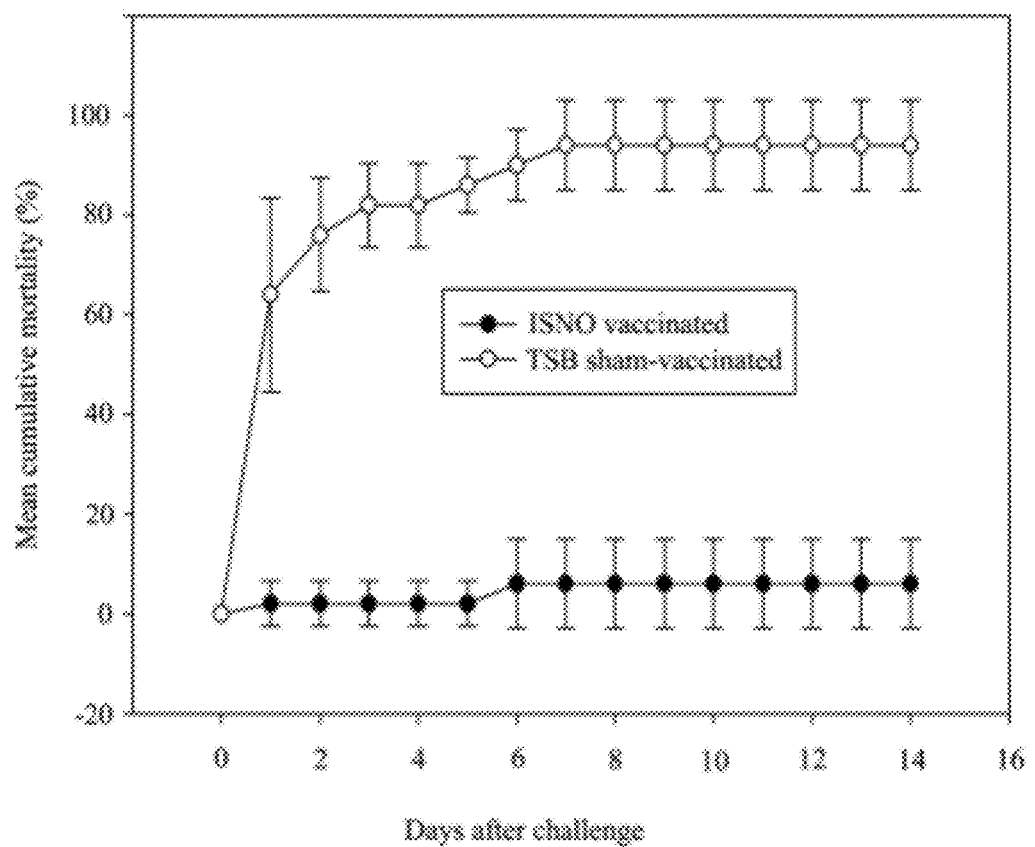
FIG. 6 is a graph showing daily mean percent cumulative mortality of Nile tilapia vaccinated through intraperitoneal injection with or without *Streptococcus iniae* ISNO and challenged with heterologous virulent strains of *Streptococcus iniae* through intraperitoneal injection. Daily mean percent cumulative mortalities were calculated from five heterologous *Streptococcus iniae* isolates (F3CB, 102F1K, 405F1K, IF6, and ARS60) challenges at 60 days post vaccination. Data are represented as mean±S.D. from the five trials.

Mortalities were recorded for about 14 days post challenge and the presence or absence of Streptococcus iniae in dead fish was determined as described earlier. Results of Streptococcus iniae challenge were presented as RPS. At approximately 60 dpv, when TSB sham-vaccinated fish were challenged by heterologous strain Streptococcus iniae ARS-98-60, approximately 80% fish died (Table 13). However, when Streptococcus iniae ISNO vaccinated fish were challenged by ARS-98-60, no fish died (Table 13). The relative percent survival of Streptococcus iniae ISNO-vaccinated fish against Streptococcus iniae ARS-98-60 challenge at about 60 dpv was 100%. At about 60 dpv, when TSB sham-vaccinated fish were challenged by heterologous strain Streptococcus iniae IF6-F3, 100% fish died (Table 13). However, when Streptococcus iniae ISNO vaccinated fish were challenged by Streptococcus iniae IF6-F3, no fish died (Table 13). The RPS of Streptococcus iniae ISNO-vaccinated fish against Streptococcus iniae IF6-F3 challenge at about 60 dpv was 100%. At about 60 dpv, when TSB sham-vaccinated fish were challenged by heterologous strain Streptococcus iniae 21101F3CB, approximately 90% fish died (Table 13). However, when Streptococcus iniae ISNO vaccinated fish were challenged by Streptococcus iniae 21101F3CB, approximately 20% fish died (Table 13). The RPS of *Streptococcus iniae* ISNO-vaccinated fish against *Streptococcus iniae* 21101F3CB challenge at about 60 dpv was 100%. At about 60 dpv, when TSB sham-vaccinated fish were challenged by heterologous strain *Streptococcus iniae* 21102F1K, 100% fish died (Table 13). However, when *Streptococcus iniae* ISNO vaccinated fish were challenged by *Streptococcus iniae* 21102F1K, approximately 10% fish died (Table 13). The RPS of *Streptococcus iniae* ISNO-vaccinated fish against *Streptococcus iniae* 21102F1K challenge at about 60 dpv was approximately 90%. At about 60 dpv, when TSB sham-vaccinated fish were challenged by heterologous strain *Streptococcus iniae* 32405F1K, 100% fish died (Table 13). However, when *Streptococcus iniae* ISNO vaccinated fish were challenged by *Streptococcus iniae* 32405F1K, no fish died (Table 13). The RPS of *Streptococcus iniae* ISNO-vac at about 60 dpv, when *Streptococcus* iniae ISNO- or TSB sham-vaccinated fish were challenged by heterologous strains of *Streptococcus iniae*, cumulative mortalities of *Streptococcus iniae* ISNO-vaccinated fish were significantly (P<0.05) lower that of TSB sham-vaccinated fish (FIG. 6).

TABLE 13

Cumulative mortality and relative percent survival (RPS) of vaccinated *tilapia* challenged with heterologous *Streptococcus iniae* isolates

| Vaccine group | Isolate used for challenge | Challenge Dose (CFU/fish) | dpv[a] | Mortality (%) | RPS[c] (%) |
|---|---|---|---|---|---|
| Sham TSB | ARS-98-60 | $4.8 \times 10^7$ | 60 | 80 | — |
| ISNO | ARS-98-60 | $4.8 \times 10^7$ | 60 | 0 | 100 |
| Sham TSB | IF6-F3 | $1.1 \times 10^8$ | 60 | 100 | — |
| ISNO | IF6-F3 | $1.1 \times 10^8$ | 60 | 0 | 100 |
| Sham TSB | 21101F3CB | $1.9 \times 10^7$ | 60 | 90 | — |
| ISNO | 21101F3CB | $1.9 \times 10^7$ | 60 | 20 | 78 |
| Sham TSB | 21102F1K | $4.8 \times 10^7$ | 60 | 100 | — |
| ISNO | 21102F1K | $4.8 \times 10^7$ | 60 | 10 | 90 |
| Sham TSB | 32405F1K | $3.6 \times 10^7$ | 60 | 100 | — |
| ISNO | 32405F1K | $3.6 \times 10^7$ | 60 | 0 | 100 |

[a]days post vaccination;
[b]intraperitoneal injection;
[c]relative percent survival Example 14

Indirect enzyme-linked immunosorbent assays (ELISA) were used to determine antibody titers using a previously described method (Shoemaker et al., J. Fish Dis., Volume 33, 537-544, 2010) with slight modifications. Briefly, 96-well ELISA plates were coated for about 1 hour at about 25 degrees C. with approximately 100 μl of *S. iniae* (ARS-98-60) antigen in carbonate buffer (CB), which was obtained from sonication and size-exclusion chromatography of *S. iniae* using approximately a 1:10 dilution in CB of the initial fraction representing the highest molecular weight fraction used. Plates were washed about three times with phosphate-buffered saline containing approximately 0.05% Tween-20 (PBS-T) and then blocked with approximately 3% bovine serum albumin in CB for about 1 hour. Following blocking, plates were washed about three times with PBS-T. Tilapia serum from five sham-vaccinated fish and five *Streptococcus iniae* vaccinated fish at different time points (each serum was tested in triplicate) was then added to the plate at about a 1:20 dilution in PBS-T. Serum was incubated for about 30 minutes followed by washing three times with PBS-T. Monoclonal anti-tilapia immunoglobulin (Shoemaker et al. 2010, supra) was diluted 1:1000 in PBS-T and then approximately added 100 μL per well was added to all wells for about 30 minutes. Following washing three times in PBS-T, approximately 100 μl of Monoclonal sheep anti-mouse IgG peroxidase conjugate at approximately 1:5000 dilution in PBS-T was added and incubated for about 15 minutes. Plates were then washed three times with PBS-T. Approximately 100 μl substrate tetramethylbenzidine (Pierce, Rockford, Ill.) was added. After about 15 minutes, the reaction was terminated by adding approximately 50 μl of approximately 3M $H_2SO_4$ to each well and the absorbance was read at approximately 450 nm using a BioRad 680 microplate reader (BioRad, Hercules, Calif.). Serum of *S. iniae*-infected fish post 28 days vaccination was used as a positive control and PBS was used as a negative control and both were included on each plate as assay controls.

Figure 7:
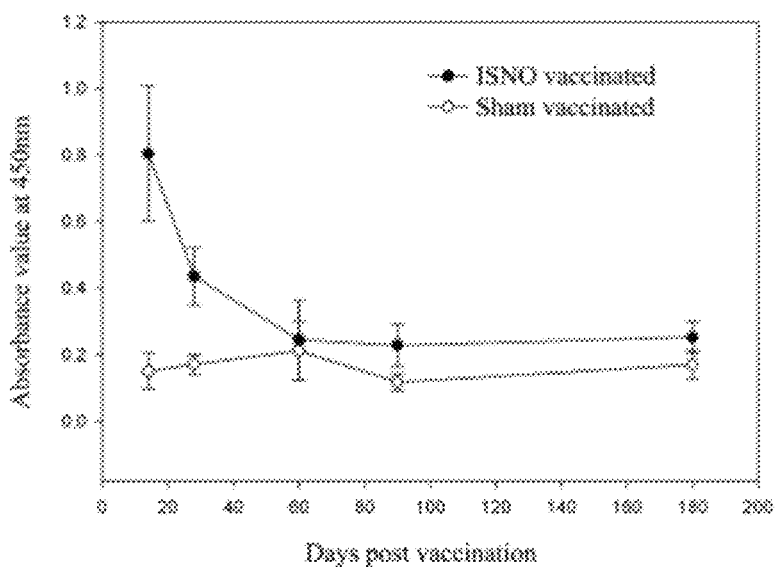
FIG. 7 is a graph showing antibody titres of pre-challenged fish vaccinated with or without *Streptococcus iniae* ISNO. Data are represented as mean±S.D. from tthree replicates.

ELISA results revealed that sham-vaccinated fish had absorbance readings similar to that of the negative control PBS at different time points. In ISNO vaccinated fish, the highest antibody titer was at about 14 days post vaccination, followed by a decline at about 28 days post vaccination and a further declines at about 60, 90 and 180 days post vaccination. At about 14 days post vaccination (pre-challenge), ISNO vaccinated tilapia produced significantly (P<0.001) higher antibody titer than TSB sham vaccinated tilapia (FIG. 7). At about 28 days post vaccination, antibody titer of ISNO vaccination vaccinated tilapia was lower than at about 14 days post vaccination. However, ISNO vaccinated tilapia still produced significantly (P 0.001) higher antibody titers than TSB sham vaccinated tilapia at about 28 days post vaccinated (FIG. 7). Antibody titers of ISNO vaccinated fish at about 60, 90, and 180 days post vaccination were all lower than that at about 14 and 28 days post vaccination. The antibody titer was not significantly different (P>0.05) between ISNO vaccinated fish and TSB sham vaccinated fish at about both 60 and 180 days post vaccination (FIG. 7).

Example 15

To develop vaccines using a novobiocin-like antibiotic, *Streptococcus agalactiae* was attenuated with a novobiocin-like chemical, coumermycin A1. Eight *Streptococcus agalactiae* isolates obtained from different fish species exhibiting clinical streptococcal disease and from different geographical regions were used for the induction of coumermycin resistance (Table 14). The archived isolates were recovered from frozen stocks (2 mL aliquots stored at −80° C.) and grown in tryptic soy broth (TSB) (Fisher Scientific, Pittsburgh, Pa.) for about 24 h at approximately 28° C. Coumermycin A1 was purchased from Promega (Madison, Wis.). All strains were cultured in tryptic soy broth (TSB) containing different concentrations of coumermycin for about 24 to about 48 h at approximately 28° C. The initial concentration of coumermycin that allowed overnight growth of *Streptococcus agalactiae* was approximately 1 ng/ml. Approximately 100 of that overnight culture was added into approximately 1 ml of tryptic soy broth containing 2 ng/ml of coumermycin. If the cells were able to grow in tryptic soy broth containing 2 ng/ml of coumermycin, approximately 10 μl of the overnight culture containing coumermycin at concentration of 2 ng/ml was then added into approximately 1 ml of tryptic soy broth containing 4 ng/ml of coumermycin. However, if the cells from the overnight culture at concentration of 1 ng/ml of coumermycin were unable to grow in tryptic soy broth containing 2 ng/ml of coumermycin, then approximately 10 μl of the overnight culture containing coumermycin at concentration of 1 ng/ml was added into approximately 1 ml of tryptic soy broth containing coumermycin equal to or higher than 1 ng/ml but less than 2 ng/ml. This process was repeated again and again until the cells were able to grow in culture media containing coumermycin at concentration of approximately 5000 ng/ml. After about 20 passages of *Streptococcus agalactiae* in TSB culture media containing same or higher concentration of coumermycin, all nine *Streptococcus agalactiae* strains were able grow in TSB containing approximately 5 µg/ml of coumermycin.

TABLE 14

*Streptococcus agalactiae* isolates used in this study

| Isolate designation | Year isolated | Location | Species of fish |
|---|---|---|---|
| Sag2/BZTN039HK | 2003 | Brazil | *Oreochromis niloticus* |
| Sag3/1SBHK | 2002 | Kuwait | *Dicentrarchus labrax* |
| Sag-4/DM | 2001 | Kuwait | *Tursiops truncatus* |
| Sag-5/BZTN031 | 2003 | Brazil | *Oreochromis niloticus* |
| Sag-7/7BREID | 2007 | Idaho, USA | *Oreochromis* spp. |
| Sag-8/H90503 | 2005 | Louisiana, USA | *Oreochromis* spp. |
| Sag-9/h05108A | 2005 | Louisiana, USA | *Morone saxatilis* × *M. chrysops* |
| Sag-10/F2BRFS | 2007 | Idaho, USA | *Oreochromis* spp. |
| Sag-12/2BRE | 2007 | Ecuador | *Oreochromis* spp. |

The nine parent and novobiocin-resistant *Streptococcus agalactiae* strains were then grown on 5% sheep blood agar plates (Thermo Fisher Scientific Remel Products, Lenexa, Kans.) for bacterial identification. Bacteria isolates were identified by gas chromatography analysis of fatty acid methyl ester using MIDI microbial identification system (MIDI, Newwark, Dalaware) according to established procedures (Shoemaker et al. 2005. J Aqua Animal Health Volume 17, 267-274). Gas chromatography analysis of fatty acid methyl ester using MIDI microbial identification system confirmed that the parent and coumermycin-resistant isolates were *Streptococcus agalactiae*.

Figure 8:
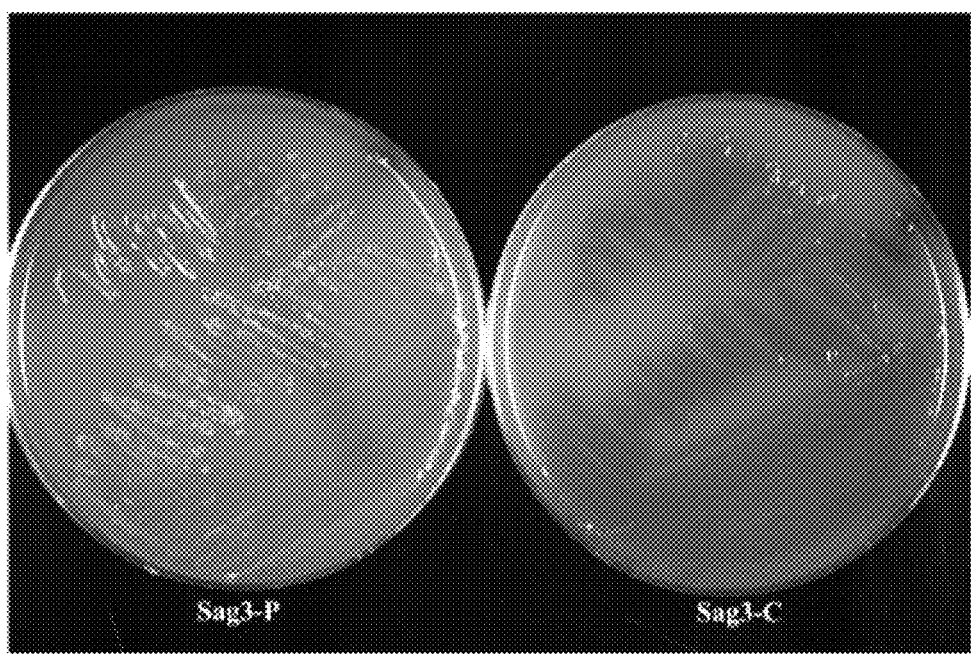
FIG. 8 is a photograph showing growth of parent *Streptococcus agalactiae* Sag3P and coumermycin-resistant *Streptococcus agalactiae* Sag3C on 5% sheep blood agar plates. The two strains were streaked out onto 5% sheep blood agar plates and incubated at 27° C. for 24 h.

When parent *Streptococcus agalactiae* Sag3 isolate and coumermycin-resistant *Streptococcus agalactiae* Sag3C were plated onto 5% sheep blood agar plates, parent *Streptococcus agalactiae* Sag3 appeared to grow much faster than the coumermycin-resistant mutant *Streptococcus agalactiae* Sag3C (FIG. 8).

Example 16

The virulence of coumermycin-resistant *Streptococcus agalactiae* isolates were compared to their parent isolates. All parent and coumermycin-resistant *Streptococcus agalactiae* isolates were cultured overnight in tryptic soy broth (TSB) at approximately 28° C. An optical density (OD) of approximately 1.0 of the bacterial cultures was measured at approximately 540 nm using Thermospectronic spectrophotmer (Fisher Scientific, Pittsburgh, Pa.). Serial dilutions (in triplicates) of each isolate were prepared in TSB and approximately 100 µL of serially diluted *Streptococcus agalactiae* were plated onto TSA plates. After about 18 h incubation at approximately 28° C., the average number of CFU/mL was calculated for all isolates. Approximately $3.6 \times 10^7$ CFU/fish of each parent and coumermycin-resistant isolate was exposed to Nile tilapia, with a mean weight of about 20 grams, through intraperitoneal injection. All fish used in this study were male tilapia from the USDA ARS Aquatic Animal Health Research facility located at Auburn, Ala. Fish were acclimated in flow-through 57-L aquaria supplied with approximately 0.5 L h$^{-1}$ dechlorinated water for about 10 days prior to experiments. A 12:12 h light:dark period of was maintained, and supplemental aeration was supplied by an air stone. Fish were fed approximately 3% body weight daily with commercial dry fish food. During the experiment, the mean dissolved oxygen was approximately 5.6 mg L–1, temperature was approximately 26° C., pH was about 7.1 and hardness was approximately 100 mg L–1. Mortalities were recorded for 14 days post exposure to *Streptococcus agalactiae*. Virulence data of both parent and coumermycin-resistant isolates of *Streptococcus agalactiae* are shown in Table 15.

When coumerymycin-resistant *Streptococcus agalactiae* isolates were intraperitoneally injected to Nile tilapia, all nine isolates caused no mortality. However, when injected at similar dose, their respective parent isolates caused 100, 70, 80, 90, 80, 70, 100, 100, and 20% mortality, respectively (Table 15). The most virulent parent *Streptococcus agalactiae* isolates were Sag2, Sag9, and Sag 10, which killed 100% of Nile tilapia at the dose of approximately $3.6 \times 10^7$ CFU per fish (Table 15).

TABLE 15

Virulence of parent and coumermycin-resistant isolates of *Streptococcus agalactiae* to Nile *tilapia* by intraperitoneal injection

| Isolate name | Mortality (%) |
|---|---|
| Sag2-C[a] | 0 |
| Sag2-P[b] | 100 |
| Sag3-C | 0 |
| Sag3-P | 70 |
| Sag4-C | 0 |
| Sag4-P | 80 |
| Sag5-C | 0 |
| Sag5-P | 90 |
| Sag7-C | 0 |
| Sag7-P | 80 |
| Sag8-C | 0 |
| Sag8-P | 70 |
| Sag9-C | 0 |
| Sag9-P | 100 |
| Sag10-C | 0 |
| Sag10-P | 100 |
| Sag12-C | 0 |
| Sag12-P | 20 |

[a]C stands for coumermycin-resistant isolate;
[b]P stands for parent isolate.

Example 17

Nile tilapia were vaccinated with coumermycin-resistant *Streptococcus agalactiae* followed with a challenge by the virulent parent isolate. Attenuated coumermycin-resistant *Streptococcus agalactiae* vaccines were cultured in TSB at approximately 28° C. at about 125 rpm overnight before vaccination. Fish were vaccinated by intraperitoneal injection at dose of approximately $3.6 \times 10^7$ CFU per fish in a total volume of approximately 100 µl for each vaccine using ten fish per vaccine. As sham-vaccination controls, approximately 100 µl of TSB were injected into ten fish total. At about 21 days post vaccination (dpv), fish were challenged by parent isolate of *Streptococcus agalactiae* through intraperitoneal injection. Mortalities were recorded for about 14 days post challenge. Results of *Streptococcus agalactiae* challenge were presented as relative percent survival (RPS).

Figure 9:
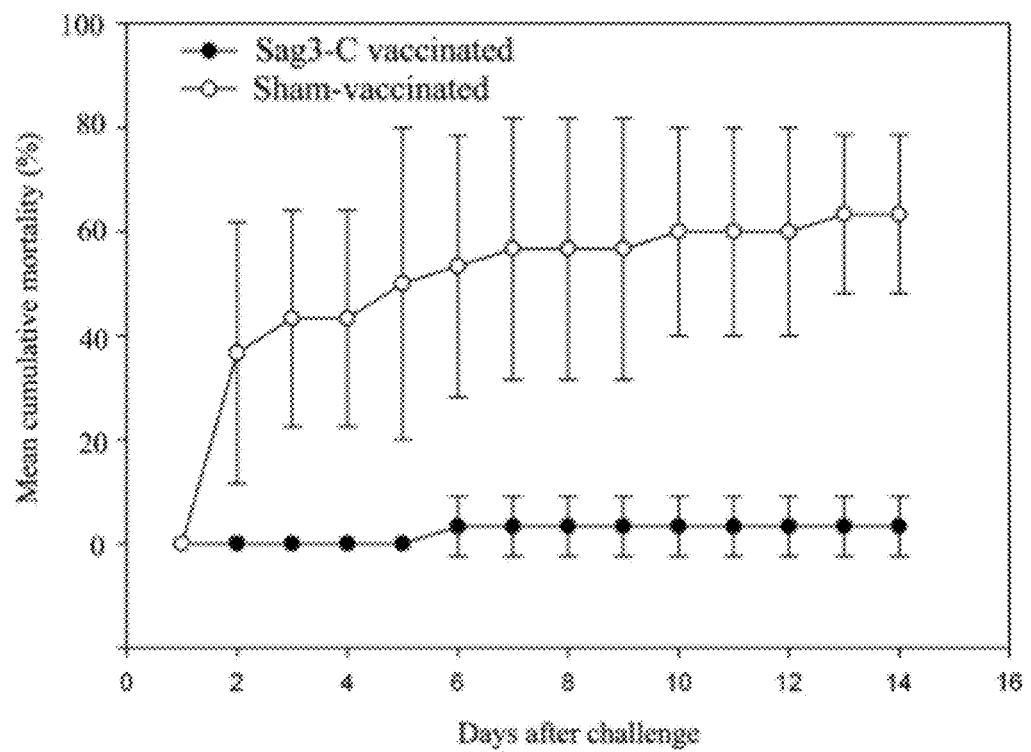
FIG. 9 is a graph showing daily mean percent cumulative mortality of Nile tilapia vaccinated with *Streptococcus agalactiae* Sag3C through intraperitoneal injection and challenged by virulent parent strain of *Streptococcus iniae* Sag3P through intraperitoneal injection. Daily mean percent cumulative mortalities were calculated from three vaccination trials (i.e., 14, 21, and 60 days post vaccination). Data are represented as mean±S.D. from the three trials.
Figure 10:
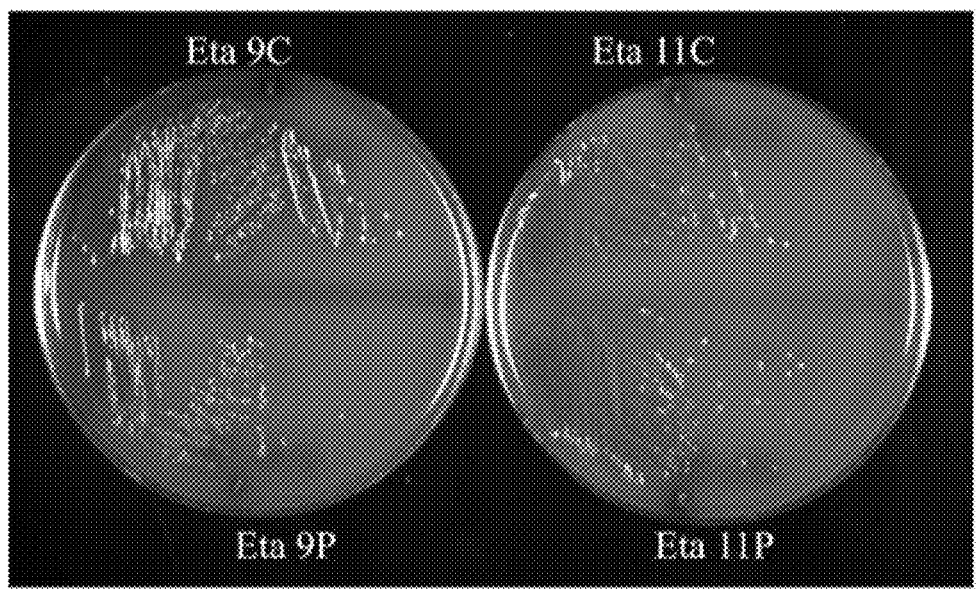
FIG. 10 is a graph showing the growth of the coumermycin-resistant *Edwardsiella tarda* Eta9C, the virulent parent *E. tarda* Eta9P, the coumermycin-resitant *E. tarda* Eta11C, and the virulent parent *E. tarda* Eta11P on 5% sheep blood agar plates. Similar amount of the parent and mutant strains were plated out onto the 5% sheep blood agar plates and incubated at 27° C. for 24 h.
Figure 11:
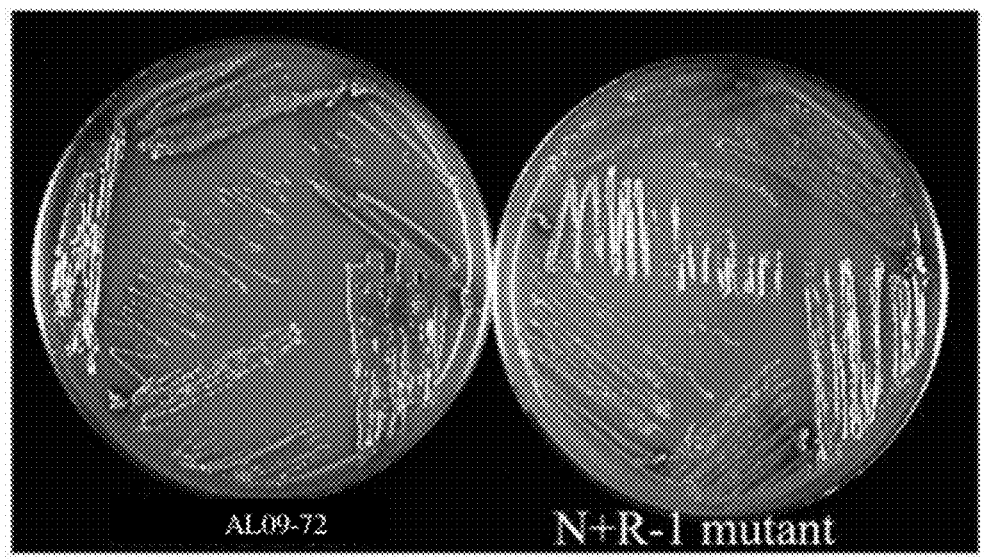
FIG. 11 is a photograph showing growth of *Aeromonas hydrophila* AL09-72 (AL #1) and *Aeromonas hydrophila* N+R−1 on 5% sheep blood agar plates. The two strains were streaked out onto 5% sheep blood agar plates and incubated at 27° C. for 24 h. Picture shown is a representative of four replicates of growth experiment on 5% sheep blood agar plates.
Figure 12:
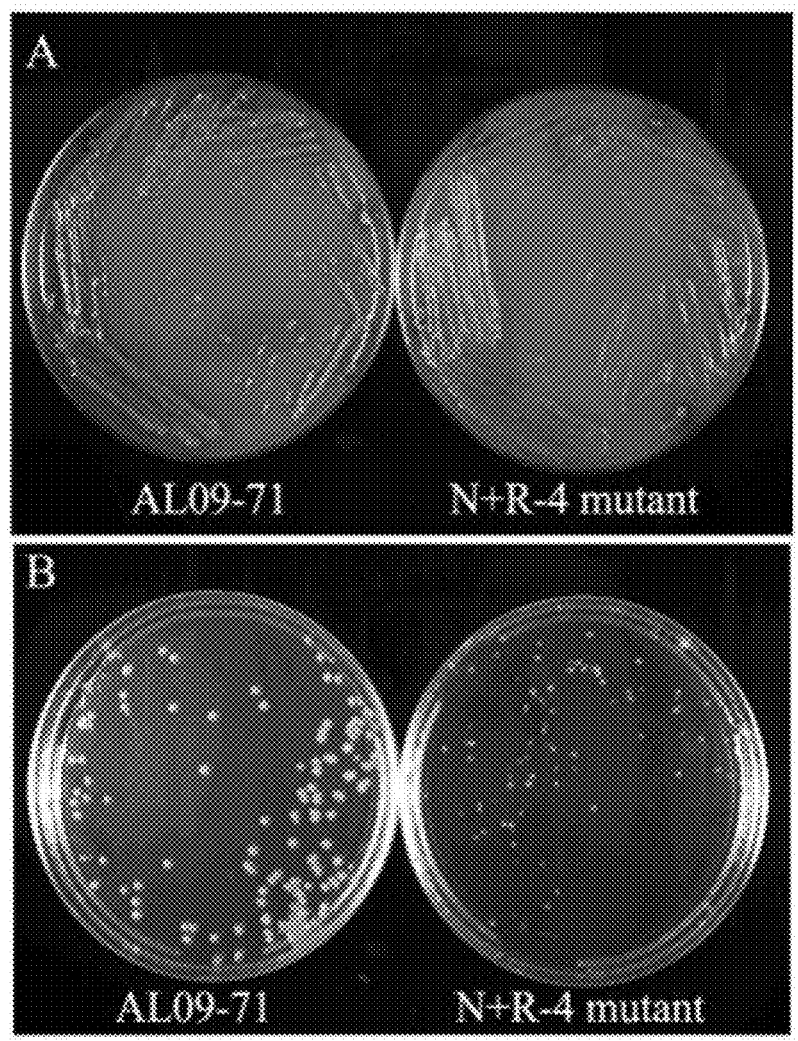
FIGS. 12A and 12B are photographs showing growth of *Aeromonas hydrophila* AL09-71 (AL#4) and *Aeromonas hydrophila* N+R−4 on tryptic soy agar plates. The two strains were either streaked out onto 5% sheep blood agar plates (FIG. 12A) or plated onto tryptic soy agar plates by spreading 100 ul overnight culuture onto the surface of the plate (FIG. 12B) and incubated at 27° C. for approximately 24 h.
Figure 13:
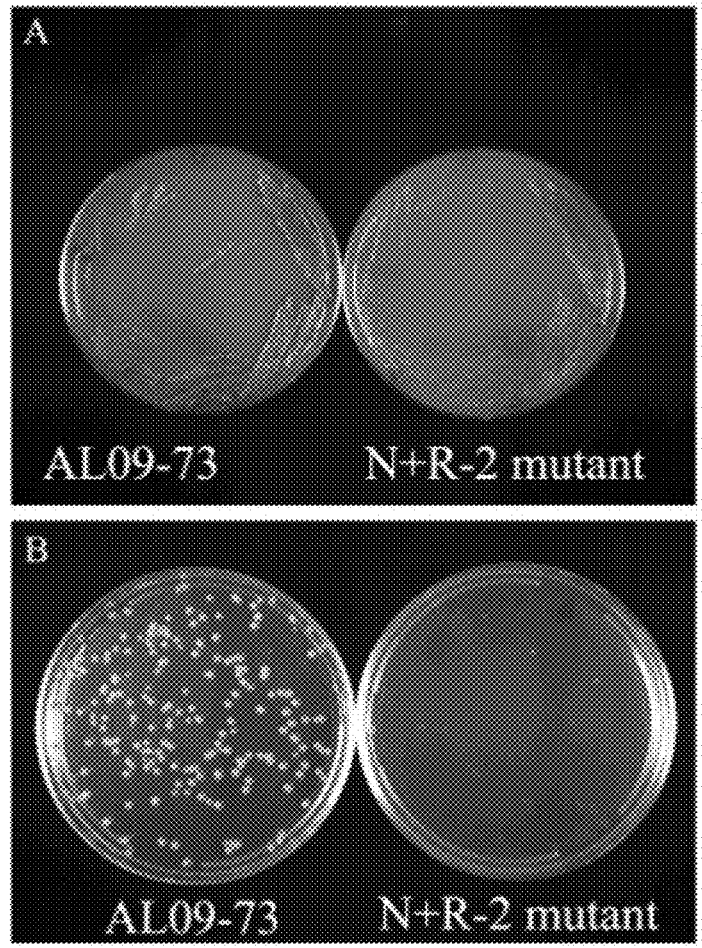
FIGS. 13A and 13B are photographs showing growth of *Aeromonas hydrophila* AL09-73 (AL #2) and *Aeromonas hydrophila* N+R−2 on tryptic soy agar plates. The two strains were either streaked out onto 5% sheep blood agar plates (FIG. 13A) or plated out onto tryptic soy agar plates by spreading 100 ul overnight culuture onto the surface of the plate (FIG. 13B) and incubated at 27° C. for approximately 24 h.
Figure 14:
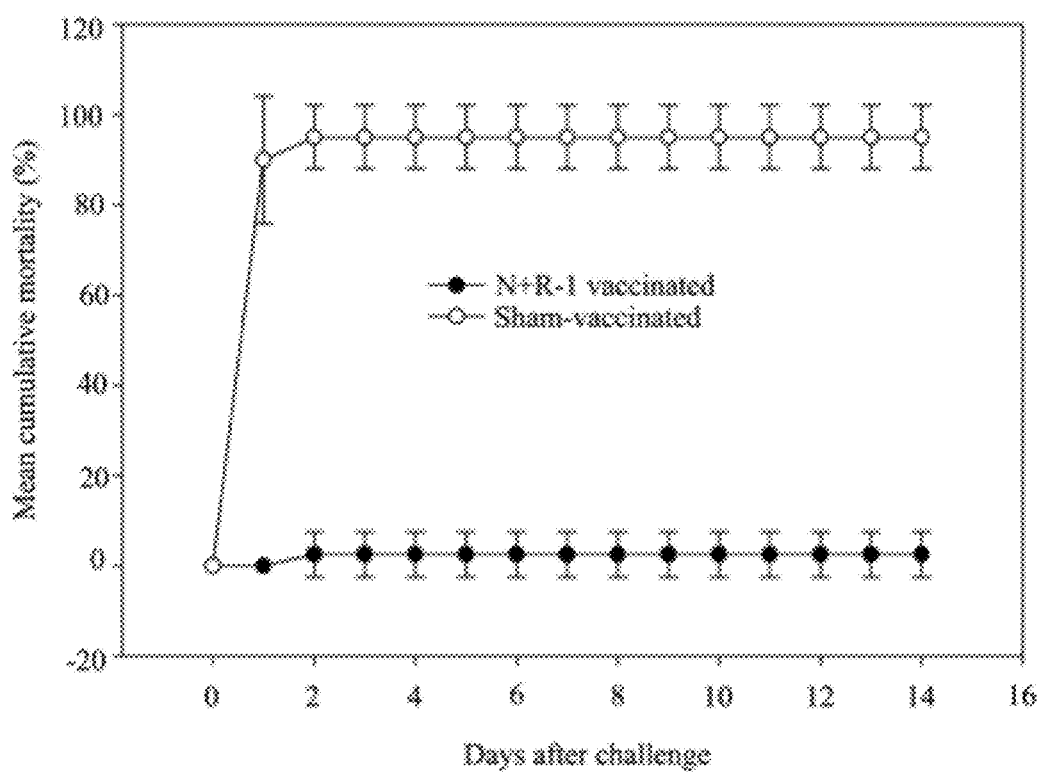
FIG. 14 is a graph showing daily mean percent cumulative mortality of *Aeromonas hydrophila* N+R−1 vaccinated channel catfish through intraperitoneal injection followed by challenge with virulent *Aeromonas hydrophila* AL09-72 (AL#1) through intraperitoneal injection. Daily mean percent cumulative mortalities were calculated from four vaccination doses/trials of approximately $5\times10^4$, $1\times10^5$, $2\times10^5$, and $4\times10^5$ CFU/fish. Data are represented as mean±S.D. from the four trials.
Figure 15:
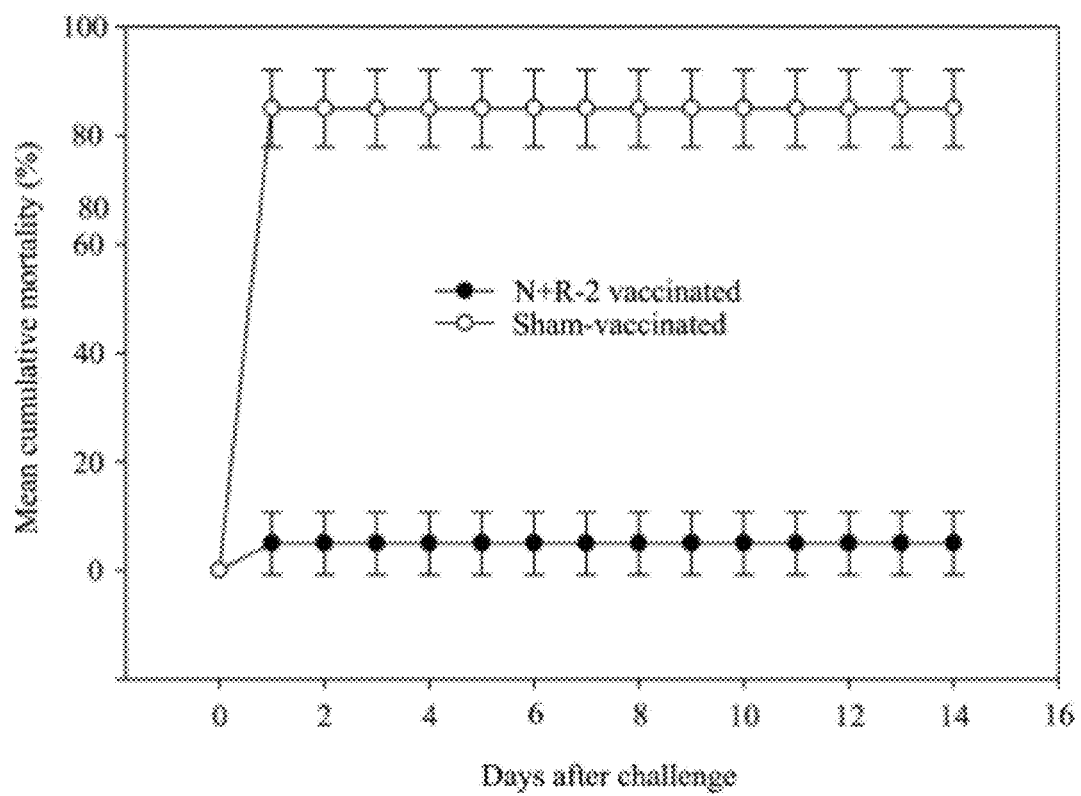
FIG. 15 is a graph showing the daily mean percent cumulative mortality of *Aeromonas hydrophila* N+R−1 vaccinated Nile tilapia through intraperitoneal injection followed by challenge with virulent *Aeromonas hydrophila* AL09-72 (AL#1) through intraperitoneal injection. Daily mean percent cumulative mortalities were calculated from two vaccination doses/trials ($1.4\times10^7$ and $1.4\times10^8$ CFU/fish). Data are represented as mean±S.D. from the two trials.
Figure 16:
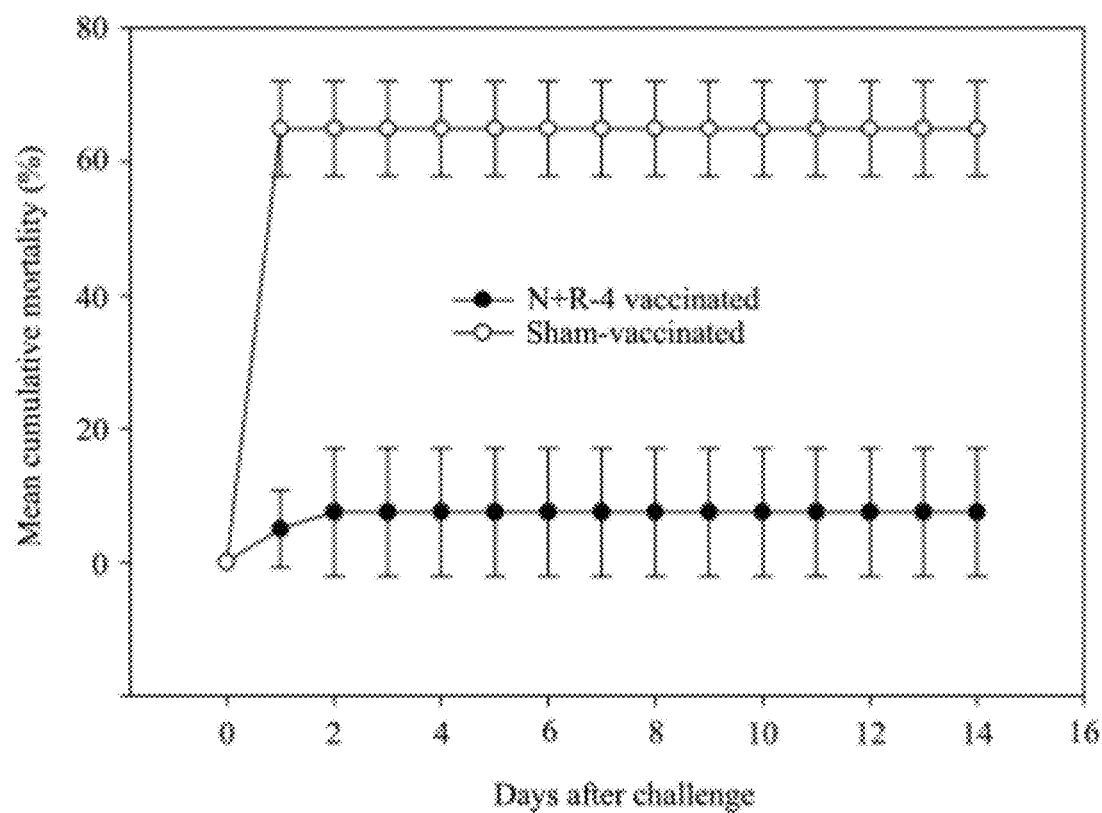
FIG. 16 is a graph showing the daily mean percent cumulative mortality of *Aeromonas hydrophila* N+R−4 intraperitoneally injection vaccinated channel catfish challenged by virulent *Aeromonas hydrophila* AL09-71 (AL#4) through intraperitoneal injection. Daily mean percent cumulative mortalities were calculated from four vaccination doses/trials ($4.75\times10^4$, $9.5\times10^4$, $1.9\times10^5$, and $3.8\times10^5$ CFU/fish). Data are represented as mean±S.D. from the four trials.

When coumermycin-resistant *Streptococcus agalactiae* Sag3C(NRRL B-50460)-vaccinated fish were challenged by its virulent parent isolate *Streptococcus agalactiae* Sag3P at approximately 21 dpv, relative percent survival of vaccinated fish was 100% (Table 16 and FIG. 9). However, when other coumermycin-resistant *Streptococcus agalactiae* mutant vaccinated fish were challenged by its virulent parent isolate, RPS value at approximately 21 dpv was all below approximately 10% (Table 16).

TABLE 16

Cumulative mortality and relative percent survival (RPS) of vaccinated tilapia challenged with virulent parent isolates

| Vaccine group | Vaccination dose (CFU/fish) | Isolate used for challenge | Challenge Dose (CFU/fish) | d.p.v.[a] | Mortality (%) | RPS[b] (%) |
|---|---|---|---|---|---|---|
| Sham TSB | — | Sag2-P[d] | $3.6 \times 10^7$ | 21 | 100 | — |
| Sag2-C[c] | $3.6 \times 10^7$ | Sag2-P | $3.6 \times 10^7$ | 21 | 90 | 10 |
| Sham TSB | — | Sag3-P | $3.6 \times 10^7$ | 21 | 80 | — |
| Sag3-C | $3.6 \times 10^7$ | Sag3-P | $3.6 \times 10^7$ | 21 | 0 | 100 |
| Sham TSB | — | Sag4-P | $3.6 \times 10^7$ | 21 | 40 | — |
| Sag4-C | $3.6 \times 10^7$ | Sag4-P | $3.6 \times 10^7$ | 21 | 50 | 0 |
| Sham TSB | — | Sag5-P | $3.6 \times 10^7$ | 21 | 100 | — |
| Sag5-C | $3.6 \times 10^7$ | Sag5-P | $3.6 \times 10^7$ | 21 | 100 | 0 |
| Sham TSB | — | Sag7-P | $3.6 \times 10^7$ | 21 | 80 | — |
| Sag7-C | $3.6 \times 10^7$ | Sag7-P | $3.6 \times 10^7$ | 21 | 100 | 0 |
| Sham TSB | — | Sag8-P | $3.6 \times 10^7$ | 21 | 40 | — |
| Sag8-C | $3.6 \times 10^7$ | Sag8-P | $3.6 \times 10^7$ | 21 | 60 | 0 |
| Sham TSB | — | Sag9-P | $3.6 \times 10^7$ | 21 | 100 | — |
| Sag9-C | $3.6 \times 10^7$ | Sag9-P | $3.6 \times 10^7$ | 21 | 100 | 0 |
| Sham TSB | — | Sag10-P | $3.6 \times 10^7$ | 21 | 100 | — |
| Sag10-C | $3.6 \times 10^7$ | Sag10-P | $3.6 \times 10^7$ | 21 | 100 | 0 |
| Sham TSB | — | Sag12-P | $3.6 \times 10^7$ | 21 | 20 | — |
| Sag12-C | $3.6 \times 10^7$ | Sag12-P | $3.6 \times 10^7$ | 21 | 60 | 0 |

[a]days post vaccination;
[b]relative percent survival;
[c]coumermycin-resistant isolate;
[d]virulent parent isolate Example 18

The efficacy of *Streptococcus agalactiae* Sag3C against homologous *Streptococcus agalactiae* challenge was tested in Nile tilapia. Both parent and coumermycin-resistant mutant *Streptococcus agalactiae* Sag3C were cultured in TSB at approximately 28° C. at about 125 rpm overnight before vaccination or challenge.

Vaccination of *Streptococcus agalactiae* Sag3C was performed at vaccination dose of approximately $3.6\times10^7$ CFU in a total volume of approximately 0.1 ml per fish through intraperitoneal injection. Sham vaccination was performed by injecting approximately 0.1 ml of tryptic soy broth to each fish. At about 14 and 60 dpv, ten fish from each vaccination group (sham- or *Streptococcus agalactiae* Sag3C-vaccinated) at each time point were challenged by its parent isolate *Streptococcus agalactiae* Sag3P (homologous isolate) at dose of approximately $3.6\times10^7$ CFU per fish through intraperitoneal injection. Mortalities were recorded for about 14 days post challenge. Results of *Streptococcus Streptococcus agalactiae* challenge were presented as RPS.

At about 14 dpv, when TSB sham-vaccinated fish were challenged by its virulent parent strain *Streptococcus agalactiae* Sag3P, apprxoimatley 60% fish died (Table 17). However, when *Streptococcus agalactiae* Sag3C vaccinated fish were challenged by its virulent parent strain *Streptococcus agalactiae* Sag3P, no fish died (Table 17). The relative percent survival of *Streptococcus agalactiae* Sag3C-vaccinated fish at about 14 dpv was 100% (Table 17). At about 60 dpv, when TSB sham-vaccinated fish were challenged by virulent strain *Streptococcus agalactiae* Sag3P, approximatgley 50% fish died (Table 17). However, when *Streptococcus agalactiae* Sag3C vaccinated fish were challenged by its virulent parent strain *Streptococcus agalactiae* Sag3P, only about 10% fish died (Table 17). The relative percent survival of vaccinated fish at about 60 dpv was approximately 80% (Table 17).

When fish were challenged by virulent parent strain *Streptococcus agalactiae* Sag3P, cumulative mortalities of virulent parent strain *Streptococcus agalactiae* Sag3C-vaccinated fish at different time points were significantly (P<0.05) lower that of TSB sham-vaccinated fish (FIG. 9).

TABLE 17

Cumulative mortality and relative percent survival (RPS) of vaccinated Nile *tilapia* challenged with virulent *Streptococcus agalactiae*

| Vaccine group | Vaccination dose (CFU/fish) | Challenge Dose (CFU/fish) | d.p.v.[a] | Mortality (%) | RPS[c] (%) |
|---|---|---|---|---|---|
| Sham TSB | — | $3.6 \times 10^7$ | 14 | 60 | — |
| Sag3C | $3.6 \times 10^7$ | $3.6 \times 10^7$ | 14 | 0 | 100 |
| Sham TSB | — | $3.6 \times 10^7$ | 60 | 50 | — |
| Sag3C | $3.6 \times 10^7$ | $3.6 \times 10^7$ | 60 | 10 | 80 |

[a]days post vaccination;
[b]intraperitoneal injection;
[c]relative percent survival

Example 19

To develop vaccines using a novobiocin-like antibiotic, *Edwardsiella tarda* was attenuated with a novobiocin-like chemical, coumermycin A1. Eight *Edwardsiella tarda* isolates obtained from different fish species exhibiting clinical enteric septicemia collected from different geographical regions were used for the induction of coumermycin resistance (Table 18). The archived isolates were recovered from frozen stocks (2 mL aliquots stored at −80° C.) and grown in tryptic soy broth (TSB) (Fisher Scientific, Pittsburgh, Pa.) for sabout 24 h at approximately 28° C. Coumermycin A1 was purchased from Promega (Madison, Wis.). All strains were cultured in tryptic soy broth (TSB) containing different concentrations of coumermycin for about 24 to about 48 h at approximately 28° C. The initial concentration of coumermycin that allowed overnight growth of *Edwardsiella tarda* was approximately 312.5 ng/ml. Approximately 10 µl of that overnight culture was added into approximately 1 ml of tryptic soy broth containing 625 ng/ml of coumermycin. If the cells were able to grow in tryptic soy broth containing 625 ng/ml of coumermycin, approximately 10 µl of the overnight culture containing coumermycin at concentration of 625 ng/ml was then added into approximately 1 ml of tryptic soy broth containing 1250 ng/ml of coumermycin. However, if the cells from the overnight culture at concentration of 312.5 ng/ml of coumermycin were unable to grow in tryptic soy broth containing 625 ng/ml of coumermycin, then approximately 10 µl of the overnight culture containing coumermycin at concentration of 1 ng/ml was added into approximately 1 ml of tryptic soy broth containing coumermycin equal to or higher than 312.5 ng/ml but less than 625 ng/ml. This process was repeated again and again until the cells were able to grow in culture media containing coumermycin at concentration of approximately 640 µg/ml. After about 20 passages of *Edwardsiella tarda* in TSB culture media containing same or higher concentration of coumermycin, all eight *Edwardsiella tarda* strains were able grow in TSB containing approximately 640 μg/ml of coumermycin.

The eight parent and coumermycin-resistant *Edwardsiella tarda* strains were then grown on 5% sheep blood agar plates (Thermo Fisher Scientific Remel Products, Lenexa, Kans.) for bacterial identification. Bacteria isolates were identified by gas chromatography analysis of fatty acid methyl ester using MIDI microbial identification system (MIDI, Newwark, Dalaware) according to established procedures (Shoemaker et al. 2005. J Aqua Animal Health Volume 17, 267-274). Gas chromatography analysis of fatty acid methyl ester using MIDI microbial identification system confirmed that parent and coumermycin-resistant mutants were all *Edwardsiella tarda* isolates.

When parent *Edwardsiella tarda* Eta9P or Eta11P isolate and coumermycin-resistant *Edwardsiella tarda* Eta9C or Eta11C were plated onto 5% sheep blood agar plates, parents and the coumermycin-resistant mutants of *Edwardsiella tarda* appeared to have the same growth rate (FIG. 10).

TABLE 18

*Edwardsiella tarda* isolates used in this study

| Isolate designation | Year isolated | Location | Species of fish |
|---|---|---|---|
| Eta1/FL6-60 | 2003 | Florida, USA | *Ictalurus punctatus* |
| Eta2/RET04 | 2003 | Florida, USA | *Ictalurus punctatus* |
| Eta4/AU9824 | 1998 | Alabama, USA | *Ictalurus punctatus* |
| Eta7/CFBRAU | 1998 | Alabama, USA | *Ictalurus punctatus* |
| Eta8/TNBRAU | 2005 | Alabama, USA | *Oreochromis* spp. |
| Eta9/ALHSBK03 | 2003 | Alabama, USA | *Morone saxatilis* × *M. chrysops* |
| Eta10/AU97052 | 1997 | Alabama, USA | *Ictalurus punctatus* |
| Eta11/AL9368B | 1993 | Alabama, USA | *Ictalurus punctatus* |

Example 20

The virulence of coumermycin-resistant *Edwardsiella tarda* mutants were compared to their parent isolates. All parent and coumermycin-resistant *Edwardsiella tarda* isolates were cultured overnight in tryptic soy broth (TSB) at approximately 28° C. An optical density (OD) of about 1.0 of the bacterial cultures was measured at approximately 540 nm using Thermospectronic spectrophotomer (Fisher Scientific, Pittsburgh, Pa.). Serial dilutions (in triplicates) of each isolate were prepared in TSB and approximately 100 μL of serially diluted *Edwardsiella tarda* were plated onto TSA plates. After about 24 h incubation at approximately 28° C., the average number of CFU/mL was calculated for all isolates. Approximately $1\times10^8$ CFU/fish of each parent and coumermycin-resistant isolate was exposed to Nile tilapia having a mean weight of approximately 20 grams through intraperitoneal injection. All fish used in this study were male tilapia from the USDA ARS Aquatic Animal Health Research facility located at Auburn, Ala. Fish were acclimated in flow-through 57-L aquaria supplied with approximately 0.5 L $h^{-1}$ dechlorinated water for about 10 days prior to experiments. A 12:12 h light:dark period of was maintained, and supplemental aeration was supplied by an air stone. Fish were fed approximately 3% body weight daily with commercial dry fish food. During the experiment, the mean dissolved oxygen was approximately 5.6 mg L−1, temperature was approximately 26° C., pH was about 7.1 and hardness was approximately 100 mg L−1. Mortalities were recorded for about 14 days post exposure to *Edwardsiella tarda*. Virulence data of both parent and coumermycin-resistant isolates of *Edwardsiella tarda* are shown in Table 19.

When coumerymycin-resistant mutants of *Edwardsiella tarda* were intraperitoneal injected to Nile tilapia, five mutants (Eta2-C, Eta4-C, Eta11-C, Eta9-C, and Eta11-C) caused no mortality. However, when injected at similar dose, their respective parent isolates caused approximately 10, 40, 80, and 10% mortality, respectively (Table 19).

TABLE 19

Virulence of parent and coumermycin-resistant isolates of *Edwardsiella tarda* to Nile *tilapia* by intraperitoneal injection

| Isolate name | Mortality (%) |
|---|---|
| Eta1-C[a] | 20 |
| Eta1-P[b] | 60 |
| Eta2-C | 0 |
| Eta2-P | 10 |
| Eta4-C | 0 |
| Eta4-P | 40 |
| Eta7-C | 0 |
| Eta7-P | 0 |
| Eta8-C | 20 |
| Eta8-P | 30 |
| Eta9-C | 0 |
| Eta9-P | 80 |
| Eta10-C | 30 |
| Eta10-P | 70 |
| Eta11-C | 0 |
| Eta11-P | 10 |

[a]C stands for coumermycin-resistant isolate;
[b]P stands for parent isolate.

Example 21

This example shows the safety of the coumermycin-resistant mutants of *E. tarda* in channel catfish. The five coumermycin-resistant mutants *Edwardsiella tarda* were cultured overnight in tryptic soy broth (TSB) at approximately approximately 28° C. An optical density (OD) of about 1.0 of the bacterial cultures was measured at approximately 540 nm using Thermospectronic spectrophotomer (Fisher Scientific, Pittsburgh, Pa.). Serial dilutions (in triplicates) of each isolate were prepared in TSB and approximately 100 μL of serially diluted *Edwardsiella tarda* were plated onto TSA plates. After about 24 h incubation at approximately 28° C., the average number of CFU/mL was calculated for all isolates.

Approximately $1 \times 10^8$ CFU/fish of each parent and coumermycin-resistant isolate was exposed to channel catfish having a mean weight of approximately 25 grams through intraperitoneal injection. All fish used in this study were channel catfish from the USDA ARS Aquatic Animal Health Research facility located at Auburn, Ala. Fish were acclimated in flow-through 57-L aquaria supplied with approximately 0.5 L h$^{-1}$ dechlorinated water for about 10 days prior to experiments. A 12:12 h light:dark period of was maintained, and supplemental aeration was supplied by an air stone. Fish were fed approximately 3% body weight daily with commercial dry fish food. During the experiment, the mean dissolved oxygen was approximately 5.6 mg L−1, temperature was approximately 26° C., pH was about 7.1 and hardness was approximately 100 mg L−1. Mortalities were recorded for 14 days post exposure to *Edwardsiella tarda*. Virulence data of the five coumermycin-resistant mutants of *Edwardsiella tarda* to channel catfish are shown in Table 20.

When coumerymycin-resistant mutants of *Edwardsiella tarda* were intraperitoneal injected to channel catfish, three mutants (Eta7-C, Eta9-C, and Eta11-C) caused no mortality. However, when injected at similar dose, Eta2C and Eta4C killed approximately 15 and 100% channel catfish, respectively (Table 20).

TABLE 20

Virulence of the five coumermycin-resistant mutants of *Edwardsiella tarda* to channel catfish by intraperitoneal injection

| Isolate name | Mortality (%) |
|---|---|
| Eta2-C[a] | 15 |
| Eta4-C | 100 |
| Eta7-C | 0 |
| Eta9-C | 0 |
| Eta11-C | 0 |

[a]C stands for coumermycin-resistant isolate;

Example 22

To study the efficacy of the three coumermycin-resistant *E. tarda* mutants as vaccine candidates, channel catfish were vaccinated with the three coumermycin-resistant mutants (Eta7-C, Eta9-C, and Eta11-C) of *Edwardsiella tarda* through intraperitoneal injection and then challenged with virulent isolates of *Edwardsiella tarda*. Attenuated coumermycin-resistant mutants of *Edwardsiella tarda* were cultured in TSB at approximately 28° C. at about 125 rpm overnight before vaccination. Fish were vaccinated by intraperitoneal injection at dose of approximately $1\times10^8$ CFU per fish in a total volume of approximately 100 μl for each vaccine using ten fish per vaccine. As sham-vaccination controls, approxiamatelyu 100 μl of TSB were injected into ten fish. At about 14 days post vaccination (dpv), fish were challenged by two virulent isolates of *Edwardsiella tarda* through intraperitoneal injection. Mortalities were recorded for about 14 days post challenge. Results of *Edwardsiella tarda* challenge were presented as relative percent survival (RPS).

At about 14 dpv, when three coumermycin-resistant mutants (Eta7-C, Eta9-C, and Eta11-C) of *Edwardsiella tarda*-vaccinated fish were challenged by virulent isolate of *Edwardsiella tarda* LSU, relative percent survival of vaccinated fish was 100% (Table 21). At about 14 dpv, when coumermycin-resistant mutants of *Edwardsiella tarda*-vaccinated fish were challenged by virulent isolate of *Edwardsiella tarda* Eta9P, relative percent survival of coumermycin-resistant *E. tarda* Eta7C, *E. tarda* Eta9C(NRRL B-50468), and Eta11C(NRRL B-50467)-vaccinated fish were approximately 56, 78 and 100%, respectively (Table 21).

TABLE 21

Cumulative mortality and relative percent survival (RPS) of vaccinated channel catfish challenged with virulent isolates of *Edwardsiella tarda*

| Vaccine group | Vaccination dose (CFU/fish) | Isolate used for challenge | Challenge Dose (CFU/fish) | d.p.v.[a] | Mortality (%) | RPS[b] (%) |
|---|---|---|---|---|---|---|
| Sham TSB | — | Eta-LSU[d] | $5.7 \times 10^6$ | 14 | 70 | — |
| Eta7-C[c] | $1 \times 10^8$ | Eta-LSU | $5.7 \times 10^6$ | 14 | 0 | 100 |
| Eta9-C | $1 \times 10^8$ | Eta-LSU | $5.7 \times 10^6$ | 14 | 0 | 100 |
| Eta11-C | $1 \times 10^8$ | Eta-LSU | $5.7 \times 10^6$ | 14 | 0 | 100 |
| Sham TSB | — | Eta-9P[d] | $2.3 \times 10^6$ | 14 | 90 | — |
| Eta7-C[c] | $1 \times 10^8$ | Eta-9P | $2.3 \times 10^6$ | 14 | 40 | 56 |
| Eta9-C | $1 \times 10^8$ | Eta-9P | $2.3 \times 10^6$ | 14 | 20 | 78 |
| Eta11-C | $1 \times 10^8$ | Eta-9P | $2.3 \times 10^6$ | 14 | 0 | 100 |

[a]days post vaccination;
[b]relative percent survival;
[c]coumermycin-resistant isolate;
[d]virulent parent isolate

Example 23

To develop vaccines using both novobiocin-resistance and rifampicin-resistance strategy, a virulent strain of *Aeromonas hydrophila* AL#1 strain (designated AL09-72), isolated from diseased channel catfish from West Alabama during a disease outbreak in 2009, was used for the induction of novobiocin and rifampicin resistance. Initial cultures of the AL09-72 strain were grown in tryptic soy broth (TSB) containing no antibiotics at approximately 28 degrees C. for about 18-24 hours. Novobiocin sodium salt was purchased form Promega (Madison, Wis.). Rifampicin was purchased from Sigma (St. Louis, Mo.). The virulent strain of *Aeromonas hydrophila* strain AL09-72 was then subjected to selection for resistance to both novobiocin and rifampicin. The initial concentration that allowed overnight growth of *A. hydrophila* AL09-72 (AL#1) was 10 μg/ml for novobiocin and 10 μg/ml for rifampicin. Approximately 10 μl of that overnight culture was then added into approximately 1 ml of tryptic soy broth containing 20 μg/ml of novobiocin and 20 μg/ml of rifampicin. If the cells were able to grow in tryptic soy broth containing 20 μg/ml of novobiocin and rifampicin, approximately 10 μl of the overnight culture containing novobiocin and rifampicin at concentration of 20 µg/ml was then added into approximately 1 ml of tryptic soy broth containing 40 µg/ml of novobiocin and 40 µg/ml of rifampicin. However, if the cells from the overnight culture containing 10 µg/ml of novobiocin and 10 µg/ml of rifampicin were unable to grow in tryptic soy broth containing 20 µg/ml of novobiocin and 20 µg/ml of rifampicin, then approximately 10 µl of the overnight culture containing 10 µg/ml of novobiocin and 10 µg/ml of rifampicin was added into approximately 1 ml of tryptic soy broth containing novobiocin and rifampicin equal to or higher than 10 µg/ml but less than 20 µg/ml. This process was repeated multiple times until the cells were able to grow in culture media containing approximately 1600 µg/ml of novobiocin and 1600 µg/ml of rifampicin. The rifampicin and novobiocin mutated avirulent strain produced from AL09-72 is designated Aeromonas hydrophila strain N+R−1 NRRL B-50369.

Following the protocol described above, two other virulent Aeromonas hydrophila isolates, also isolated from diseased fish in 2009 during the disease outbreak in West Alabama, designated AL09-71 (also called AL#4) and AL09-73 (also called AL#2) were mutated with both rifampicin and novobiocin to avirulent forms of their virulent parents. The novobiocin and rifampicin resistant *Aeromonas hydrophila* AL#4 strain is designated as N+R−4 (NRRL B-50419), and the novobiocin and rifampicin resistant *Aeromonas hydrophila* AL#2 is designated as N+R−2 (NRRL B-50418). The three avirulent strains have been cultured in tryptic soy broth containing approximately 1600 μg/ml of rifampicin and novobiocin for more than three passages. The three avirulent strains can survive and reproduce on a media containing approximately 1600 μg/ml rifampicin and approximately 1600 μg/ml novobiocin without negative effect.

Example 24

The growth and biochemical characteristics of *Aeromonas hydrophila* N+R−1 NRRL B-50369, N+R−4 NRRL B-50419, and N+R−2 NRRL B-50418 were determined by growing the avirulent and virulent parental strains on tryptic soy agar plates. The biochemical characteristics were determined using API-20E bacterial identification test strip (Biomérieux, Durham, N.C.). NRRL B-50369, NRRL B-50419, and NRRL B-50418 grew slower on tryptic soy agar plates compared to their virulent parental strains. Biochemical analysis using API-20E bacterial identification test strip (Biomérieux, Durham N.C.) revealed that parent and the novobiocin and rifampicin-resistant mutants of *Aeromonas hydrophila* had the same biochemical profiles (Table 22). When parent *Aeromonas hydrophila* AL#1 and the novobiocin and rifampicin-resistant mutant *Aeromonas hydrophila* N+R−1 were plated on 5% sheep blood agar plates, the growth of *Aeromonas hydrophila* N+R−1 was slower than that of *Aeromonas hydrophila* AL#1 (FIG. 11). Similarly, when parent *Aeromonas hydrophila* AL#4 or AL#2 and the novobiocin and rifampicin-resistant mutant *Aeromonas hydrophila* N+R−4 or N+R−2 were plated on 5% sheep blood agar plates, the growth of the novobiocin and rifampicin-resistant mutant *Aeromonas hydrophila* N+R−4 or N+R−2 was slower than its respective parent *Aeromonas hydrophila* AL#4 or AL#2 (FIGS. 12 and 13).

TABLE 22

Results of the API-20E bacterial identification test strip for the *A. hydrophila* N + R − 1.

| | | Results (Positive or negative) | | Results (Positive or negative) | | Results (Positive or negative) | |
|---|---|---|---|---|---|---|---|
| Tests | Reactions/Enzymes | AL09-72 | N + R − 1 | AL09-71 | N + R − 4 | AL09-73 | N + R − 2 |
| ONPG | B-galactosidase | Positive | Positive | Positive | Positive | Positive | Positive |
| ADH | Arginine dihydrolase | Positive | Positive | Positive | Positive | Positive | Positive |
| LDC | Lysine decarboxylase | Negative | Negative | Negative | Negative | Negative | Negative |
| ODC | Ornithine decarboxylase | Negative | Negative | Negative | Negative | Negative | negative |
| CIT | Citrate Utilization | Positive | Positive | Positive | Positive | Positive | Positive |
| $H_2S$ | $H_2S$ Production | Negative | Negative | Negative | Negative | Negative | Negative |
| URE | Urease | Negative | Negative | Negative | Negative | Negative | Negative |
| TDA | Tryptophane deaminase | Negative | Negative | Negative | Negative | Negative | Negative |
| IND | Indole production | Positive | Positive | Positive | Positive | Positive | Positive |
| VP | Acetoin Production | Positive | Positive | Positive | Positive | Positive | Positive |
| GEL | Gelatinase | Positive | Positive | Positive | Positive | Positive | Positive |
| GLU | Fermentation/Oxidation (Gluscose) | Positive | Positive | Positive | Positive | Positive | Positive |
| MAN | Fermentation/Oxidation (mannitol) | Positive | Positive | Positive | Positive | Positive | Positive |
| INO | Fermentation/Oxidation (inositol) | Positive | Positive | Positive | Positive | Positive | Positive |
| SOR | Fermentation/Oxidation (sorbitol) | Negative | Negative | Negative | Negative | Negative | Negative |
| RHA | Fermentation/oxidation (rhamnose) | Negative | Negative | Negative | Negative | Negative | Negative |
| SAC | Fermentation/oxidation (saccharrose) | Positive | Positive | Positive | Positive | Positive | Positive |
| MEL | Fermentation/oxidation (melibiose) | Negative | Negative | Negative | Negative | Negative | Negative |
| AMY | Fermentation/oxidation (amygdalin) | Negative | Negative | Negative | Negative | Negative | Negative |
| ARA | Fermentation/oxidation (arabinose) | Positive | Positive | Positive | Positive | Positive | Positive |
| OX | Cytochrome-oxidase | Positive | Positive | Positive | Positive | Positive | Positive |

N + R − 4, and N + R − 2 strains compared to the virulent parent strains AL09-72, AL09-71 and AL09-73.

Example 25

The virulence of the three novobiocin and rifampicin-resistant mutants of *Aeromonas hydrophila* was then compared to the virulence of their parental virulent strains by intraperitoneal injection (IP) of the strains in channel catfish. Both the parent and the novobiocin and rifampicin-resistant mutants of *Aeromonas hydrophila* were cultured overnight in tyrptic soy broth (TSB) at approximately 27 degrees C. All catfish (Industry pool strain, USDA, Catfish Genetics Research Unit, Stoneville, Miss.) for this study were raised at the USDA ARS Aquatic Animal Research facility located at Auburn, Ala. and naïve to *Aeromonas hydrophila*. Intraperitoneal injection was performed by injecting different colony forming units (CFU) (See Tables 23-25) of *Aeronomas hydrophila* in a total volume of approximately 0.1 ml into catfish. Mortalities were recorded for approximately 14 days post exposure to *A. hydrophila*.

At dose of approximately $4\times10^5$ CFU per catfish, the parent *Aeromonas hydrophila* AL#1 killed 70% catfish. However, at similar dose of approximately $4\times10^5$ CFU per catfish, the mutant *Aeromonas hydrophila* N+R−1 was safe to catfish (Table 23). At dose of approximately $1\times10^5$ CFU per fish, the parent *Aeromonas hydrophila* AL#1 killed 100% catfish. However, at similar dose of approximately $1\times10^5$ CFU per fish, the mutant *Aeromonas hydrophila* N+R−1 was safe to catfish, causing no mortality (Table 23).

At dose of approximately $2.5\times10^5$ CFU per catfish, the parent *Aeromonas hydrophila* AL#2 killed 100% catfish (Table 24). However, at similar dose of approximately $2.5\times10^5$ CFU per catfish, the mutant *Aeromonas hydrophila* N+R−2 was safe to catfish, causing no mortality (Table 24). At dose of approximately $6.25\times10^4$ CFU per fish, the parent *Aeromonas hydrophila* AL#2 killed 80% catfish. However, at similar dose of approximately $6.25\times10^4$ CFU per fish, the mutant *Aeromonas hydrophila* N+R−2 was safe to catfish, causing no mortality (Table 24).

At dose of approximately $3.8\times10^5$ CFU per catfish, the parent *Aeromonas hydrophila* AL#4 killed 80% catfish (Table 25). However, at similar dose of approximately $3.8\times10^5$ CFU per catfish, the mutant *Aeromonas hydrophila* N+R−4 was safe to catfish, causing no mortality (Table 25). At dose of $4.75\times10^4$ CFU per fish, the parent *Aeromonas hydrophila* AL#4 killed 70% catfish. However, at similar dose of approximately $4.75\times10^4$ CFU per fish, the mutant *Aeromonas hydrophila* N+R−4 was safe to catfish, causing no mortality (Table 25).

TABLE 23

Virulence of N + R-1 and AL09-72 to catfish by intraperitoneal injection

| Treatment | Fish weight (g) | No. of fish | Exposure method | Amount (CFU/fish) | Mortality (%)[a] |
|---|---|---|---|---|---|
| TSB[b] control | 6.95 | 10 | injection | — | 0 |
| AL09-72 | 6.95 | 10 | injection | $4 \times 10^5$ | 70 |
| AL09-72 | 6.95 | 10 | injection | $2 \times 10^5$ | 80 |
| AL09-72 | 6.95 | 10 | injection | $1 \times 10^5$ | 100 |
| AL09-72 | 6.95 | 10 | injection | $5 \times 10^4$ | 90 |
| N + R-1 | 6.95 | 10 | injection | $4 \times 10^5$ | 0 |
| N + R-1 | 6.95 | 10 | injection | $2 \times 10^5$ | 0 |
| N + R-1 | 6.95 | 10 | injection | $1 \times 10^5$ | 0 |
| N + R-1 | 6.95 | 10 | injection | $5 \times 10^4$ | 0 |

[a]cumulative mortality was calculated at 14 days post treatment;
[b]tryptic soy broth

TABLE 24

Virulence of N + R-2 and AL09-73 to catfish by intraperitoneal injection

| Treatment | Fish weight (g) | No. of fish | Exposure method | Amount (CFU/fish) | Mortality (%)[a] |
|---|---|---|---|---|---|
| TSB[b] control | 6.95 | 10 | injection | — | 0 |
| AL09-73 | 6.95 | 10 | injection | $2.50 \times 10^5$ | 100 |
| AL09-73 | 6.95 | 10 | injection | $1.25 \times 10^5$ | 70 |
| AL09-73 | 6.95 | 10 | injection | $6.25 \times 10^4$ | 80 |
| AL09-73 | 6.95 | 10 | injection | $3.13 \times 10^4$ | 90 |
| N + R-2 | 6.95 | 10 | injection | $2.50 \times 10^5$ | 0 |
| N + R-2 | 6.95 | 10 | injection | $1.25 \times 10^5$ | 0 |
| N + R-2 | 6.95 | 10 | injection | $6.25 \times 10^4$ | 0 |
| N + R-2 | 6.95 | 10 | injection | $3.13 \times 10^4$ | 0 |

[a]cumulative mortality was calculated at 14 days post treatment;
[b]tryptic soy broth

TABLE 25

Virulence of N + R-4 and AL09-71 to catfish by intraperitoneal injection

| Treatment | Fish weight (g) | No. of fish | Exposure method | Amount (CFU/fish) | Mortality (%)[a] |
|---|---|---|---|---|---|
| TSB[b] control | 6.95 | 10 | injection | — | 0 |
| AL09-71 | 6.95 | 10 | injection | $3.80 \times 10^5$ | 80 |
| AL09-71 | 6.95 | 10 | injection | $1.90 \times 10^5$ | 80 |
| AL09-71 | 6.95 | 10 | injection | $9.50 \times 10^4$ | 80 |
| AL09-71 | 6.95 | 10 | injection | $4.75 \times 10^4$ | 70 |
| N + R-4 | 6.95 | 10 | injection | $3.80 \times 10^5$ | 0 |
| N + R-4 | 6.95 | 10 | injection | $1.90 \times 10^5$ | 0 |
| N + R-4 | 6.95 | 10 | injection | $9.50 \times 10^4$ | 0 |
| N + R-4 | 6.95 | 10 | injection | $4.75 \times 10^4$ | 0 |

[a]cumulative mortality was calculated at 14 days post treatment;
[b]tryptic soy broth

Example 26

Nile Tilapia were also injected intraperitoneally with the three vaccines to assess safety. The attenuated and wild-type *Aeromonas hydrophila* were cultured overnight in tryptic soy broth (TSB) at approximately 27 degrees C. All Nile tilapia used in this example were raised at the USDA ARS Aquatic Research facility located at Auburn, Ala. and naïve to *Aeromonas hydrophila*. Intraperitoneal injections were performed by injecting different concentrations (colony forming units or CFU) (See Tables 26-28) of *Aeromonas hydrophila*, either a virulent parent strain or an avirulent or attenuated strain, in a total volume of approximately 0.1 ml. Mortalities were recorded for about 14 days post injection. After 14 days the only mortality recorded was for fish injected with the virulent parent strains of *Aeromonas hydrophila*.

At dose of approximately $3.2\times10^8$ CFU per Nile tilapia, the parent *Aeromonas hydrophila* AL#1 killed 100% catfish. However, at similar dose of approximately $3.2\times10^8$ CFU per Nile tilapia, the mutant *Aeromonas hydrophila* N+R−1 was safe for Nile tilapia, causing no mortality (Table 26).

At dose of approximatly $2\times10^8$ CFU per Nile tilapia, the parent *Aeromonas hydrophila* AL#2 killed 100% catfish. However, at similar dose of approximately $2\times10^8$ CFU per Nile tilapia, the mutant *Aeromonas hydrophila* N+R−2 was safe for Nile tilapia, causing no mortality (Table 27).

At dose of approximately $3\times10^8$ CFU per Nile tilapia, the parent *Aeromonas hydrophila* AL#4 killed 100% catfish. However, at similar dose of approximately $3\times10^8$ CFU per Nile tilapia, the novobiocin and rifampicin resistant mutant *Aeromonas hydrophila* N+R−4 was safe for Nile tilapia, causing no mortality (Table 28).

TABLE 26

Injection of N + R-1 and AL09-72 to Nile *tilapia* by intraperitoneal injection.

| Treatment | Fish weight (g) | No. of fish | Exposure method | Amount (CFU/fish) | Mortality (%)[a] |
|---|---|---|---|---|---|
| TSB[b] control | 15 | 10 | injection | — | 0 |
| AL09-72 | 15 | 10 | injection | $3.2 \times 10^8$ | 100 |
| AL09-72 | 15 | 10 | injection | $3.2 \times 10^7$ | 0 |
| AL09-72 | 15 | 10 | injection | $3.2 \times 10^6$ | 0 |
| AL09-72 | 15 | 10 | injection | $8 \times 10^5$ | 0 |
| N + R-1 | 15 | 10 | injection | $3.2 \times 10^8$ | 0 |
| N + R-1 | 15 | 10 | injection | $3.2 \times 10^7$ | 0 |
| N + R-1 | 15 | 10 | injection | $3.2 \times 10^6$ | 0 |
| N + R-1 | 15 | 10 | injection | $8 \times 10^5$ | 0 |

[a]cumulative mortality was calculated at 14 days post treatment

TABLE 27

Injection of N + R-2 and AL09-73 to Nile *tilapia* by intraperitoneal injection.

| Treatment | Fish weight (g) | No. of fish | Exposure method | Amount (CFU/fish) | Mortality (%)[a] |
|---|---|---|---|---|---|
| TSB[b] control | 15 | 10 | injection | — | 0 |
| AL09-73 | 15 | 10 | injection | $2 \times 10^8$ | 100 |
| AL09-73 | 15 | 10 | injection | $2 \times 10^7$ | 78 |
| AL09-73 | 15 | 10 | injection | $2 \times 10^6$ | 0 |
| AL09-73 | 15 | 10 | injection | $2 \times 10^5$ | 0 |
| N + R-2 | 15 | 10 | injection | $2 \times 10^8$ | 0 |
| N + R-2 | 15 | 10 | injection | $2 \times 10^7$ | 0 |
| N + R-2 | 15 | 10 | injection | $2 \times 10^6$ | 0 |
| N + R-2 | 15 | 10 | injection | $2 \times 10^5$ | 0 |

[a]cumulative mortality was calculated at 14 days post treatment
[b]tryptic soy broth

TABLE 28

Injection of N + R-4 and AL09-71 to Nile *tilapia* by intraperitoneal injection.

| Treatment | Fish weight (g) | No. of fish | Exposure method | Amount (CFU/fish) | Mortality (%)[a] |
|---|---|---|---|---|---|
| TSB[b] control | 15 | 10 | injection | — | 0 |
| AL09-71 | 15 | 10 | injection | $3 \times 10^8$ | 90 |
| AL09-71 | 15 | 10 | injection | $3 \times 10^7$ | 70 |
| AL09-71 | 15 | 10 | injection | $3 \times 10^6$ | 0 |
| AL09-71 | 15 | 10 | injection | $3 \times 10^5$ | 0 |
| N + R-4 | 15 | 10 | injection | $3 \times 10^8$ | 0 |
| N + R-4 | 15 | 10 | injection | $3 \times 10^7$ | 0 |
| N + R-4 | 15 | 10 | injection | $3 \times 10^6$ | 0 |
| N + R-4 | 15 | 10 | injection | $3 \times 10^5$ | 0 |

[a]cumulative mortality was calculated at 14 days post treatment
[b]tryptic soy broth

Example 27

The efficacy of the three novobiocin and rifampicin-resistant mutants of *Aeromonas hydrophila* as vaccine candidates was evaluated in channel catfish. Channel catfish were vaccinated by a single IP injection with either of the three novel *Aeromonas hydrophila* (See tables 29-31 for CFU/fish). Control fish were injected with TSB as a sham-vaccination control. After about 14 days post vaccination, channel catfish were challenged by the virulent parent strains of the attenuated *Aeromonas hydrophila* used in the vaccines through IP injection. Mortalities were recorded for 14 days post challenge and results in Tables 29-31 were presented as relative percent survival (RPS).

When TSB sham vaccinated fish were challenged with the virulent parent strain AL09-72 of *Aeromonas hydrophila*, all fish died. However, the fish vaccinated with the attenuated strain of N+R−1 at concentrations of $4\times10^5$, $2\times10^5$, and $5\times10^4$ CFU/fish all lived post challenge. Fish vaccinated with N+R−1 at a concentration of $1\times10^5$ had an approximately 90% survival rate (Table 29). When catfish were challenged by virulent AL09-72, cumulative mortalities of N+R+1 vaccinated fish were significantly ($P<0.05$) lower than that of TSB sham-vaccinated fish (FIG. 14).

When TSB sham vaccinated fish were challenged with the virulent parent strain AL09-73 of *Aeromonas hydrophila*, approximately 90% fish died. However, the fish vaccinated with the attenuated strain of N+R−2 at concentrations of $2.5\times10^5$ and $1.25\times10^5$CFU/fish all lived post challenge. Fish vaccinated with N+R−2 at a concentration of $6.25\times10^4$ and $3.13\times10^4$ had an approximately 90% survival rate (Table 30). Relative survival of N+R−2 vaccinated fish at all vaccination doses were approximately 89% to approximately 100% (Table 30). When catfish were challenged by virulent AL09-73, cumulative mortalities of N+R+2 vaccinated fish were significantly ($P<0.05$) lower than that of TSB sham-vaccinated fish (FIG. 15).

When TSB sham vaccinated fish were challenged with the virulent parent strain AL09-71 of *Aeromonas hydrophila*, approximately 70% fish died. However, the fish vaccinated with the attenuated strain of N+R−4 at concentrations of $1.9\times10^5$, and $4.75\times10^4$ CFU/fish all lived post challenge (Table 31). Fish vaccinated with N+R−4 at a concentration of $3.8\times10^5$ and $9.5\times10^4$ had an approximately 90% and approximately 80% survival rate, respectively (Table 31). Relative percent survival of N+R−4 vaccinated fish at all vaccination doses was approximately 71% to approximately 100% (Table 20). When catfish were challenged by virulent AL09-71, cumulative mortalities of N+R+4 vaccinated fish were significantly lower ($P<0.05$) than TSB sham-vaccinated fish (FIG. 16).

TABLE 29

Cumulative mortality and relative percent survival (RPS) of IP vaccinated catfish challenged with AL09-72 virulent strain

| Vaccine group | Vaccination dose (CFU/fish) | Fish starting weight (g) | Challenge Dose (CFU/fish) | d.p.v.[a] | Mortality (%) | RPS[b] (%) |
|---|---|---|---|---|---|---|
| TSB[c] control | — | 6.95 | $4 \times 10^5$ | 15 | 100 | — |
| N + R − 1 | $4 \times 10^5$ | 6.95 | $4 \times 10^5$ | 15 | 0 | 100 |
| N + R − 1 | $2 \times 10^5$ | 6.95 | $4 \times 10^5$ | 15 | 0 | 100 |
| N + R − 1 | $1 \times 10^5$ | 6.95 | $4 \times 10^5$ | 15 | 10 | 90 |
| N + R − 1 | $5 \times 10^4$ | 6.95 | $4 \times 10^5$ | 15 | 0 | 100 |

[a]days post vaccination;
[b]relative percent survival;
[c]tryptic soy broth

TABLE 30

Cumulative mortality and relative percent survival (RPS) of IP vaccinated catfish challenged with AL09-73 virulent strain

| Vaccine group | Vaccination dose (CFU/fish) | Fish starting weight (g) | Challenge Dose (CFU/fish) | d.p.v.[a] | Mortality (%) | RPS[b] (%) |
|---|---|---|---|---|---|---|
| TSB[c] control | — | 6.95 | $3 \times 10^4$ | 15 | 90 | — |
| N + R − 2 | $2.50 \times 10^5$ | 6.95 | $3 \times 10^4$ | 15 | 0 | 100 |

TABLE 30-continued Cumulative mortality and relative percent survival (RPS) of IP vaccinated catfish challenged with AL09-73 virulent strain

| Vaccine group | Vaccination dose (CFU/fish) | Fish starting weight (g) | Challenge Dose (CFU/fish) | d.p.v.[a] | Mortality (%) | RPS[b] (%) |
|---|---|---|---|---|---|---|
| N + R − 2 | $1.25 \times 10^5$ | 6.95 | $3 \times 10^4$ | 15 | 0 | 100 |
| N + R − 2 | $6.25 \times 10^4$ | 6.95 | $3 \times 10^4$ | 15 | 10 | 89 |
| N + R − 2 | $3.13 \times 10^4$ | 6.95 | $3 \times 10^4$ | 15 | 10 | 89 |

[a] days post vaccination;
[b] relative percent survival;
[c] tryptic soy broth

TABLE 31

Cumulative mortality and relative percent survival (RPS) of IP vaccinated catfish challenged with AL09-71 virulent strain

| Vaccine group | Vaccination dose (CFU/fish) | Fish starting weight (g) | Challenge Dose (CFU/fish) | d.p.v.[a] | Mortality (%) | RPS[b] (%) |
|---|---|---|---|---|---|---|
| TSB[c] control | — | 6.95 | $4.75 \times 10^4$ | 15 | 70 | — |
| N + R − 4 | $3.80 \times 10^5$ | 6.95 | $4.75 \times 10^4$ | 15 | 10 | 86 |
| N + R − 4 | $1.90 \times 10^5$ | 6.95 | $4.75 \times 10^4$ | 15 | 0 | 100 |
| N + R − 4 | $9.50 \times 10^4$ | 6.95 | $4.75 \times 10^4$ | 15 | 20 | 71 |
| N + R − 4 | $4.75 \times 10^4$ | 6.95 | $4.75 \times 10^4$ | 15 | 0 | 100 |

[a] days post vaccination;
[b] relative percent survival;
[c] tryptic soy broth

Example 28

Example 27 above is repeated with Nile tilapia with the exception that tilapia were challenged approximately 28 days post vaccination with the virulent parent strains of the attenuated vaccine strains. As in Example 27, mortalities were recorded for approximately 14 days post challenge. Results of experimental challenge were presented as relative percent survival (RPS).

Figure 17:
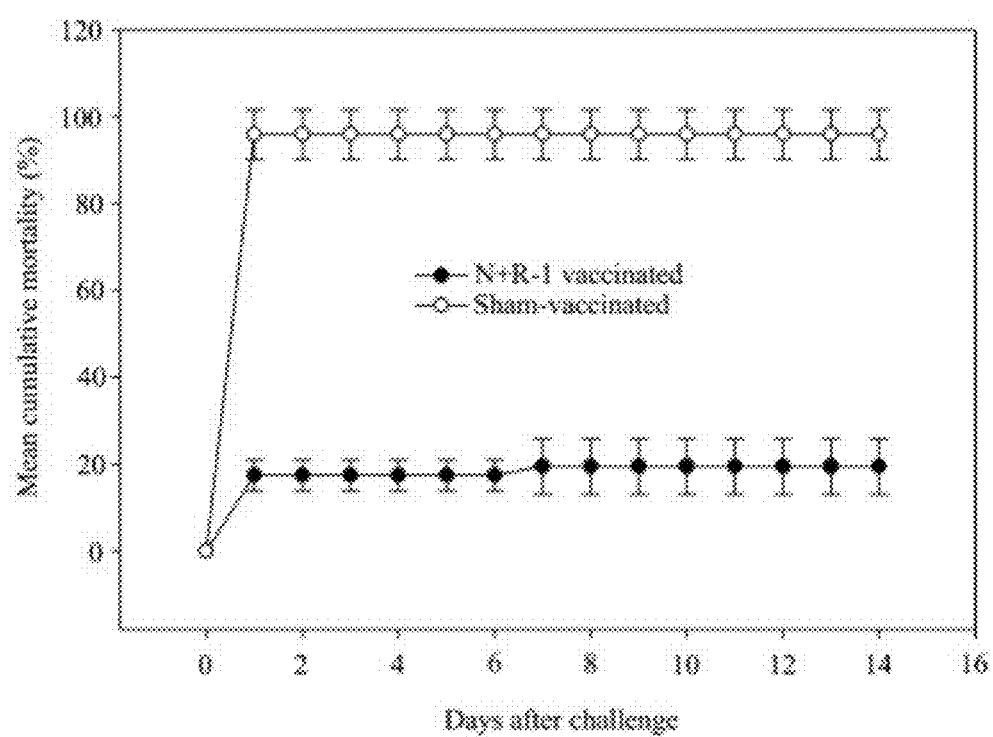
FIG. 17 is a graph showing the daily mean percent cumulative mortality of *Aeromonas hydrophila* N+R−4 intraperitoneally injection vaccinated Nile tilapia challenged by virulent *Aeromonas hydrophila* AL09-71 (AL#4) through intraperitoneal injection. Daily mean percent cumulative mortalities were calculated from three vaccination doses/trials ($1.3\times10^6$, $1.3\times10^7$, and $1.3\times10^8$ CFU/fish). Data are represented as mean±S.D. from the three trials.

The TSB sham vaccinated fish challenged with the virulent parent strain AL09-72 of *Aeromonas hydrophila* had a mortality of approximately 92 to approximately 100% (Table 32). However, the fish vaccinated with the attenuated strain of N+R−1 at concentrations of $1.4 \times 10^8$, and $1.4 \times 10^7$ CFU/fish had a mortality of approximately 15% and approximately 24% respectively (Table 32). When the vaccination dose was equal or lower than approximately $1.4 \times 10^6$ CFU/fish, RPS value was equal to or lower than approximately 30% (Table 32). When N+R−1 vaccinated Nile tilapia were challenged by virulent AL09-72, cumulative mortalities of vaccinated fish at vaccination doses of $1.4 \times 10^7$, and $1.4 \times 10^8$ CFU/fish were significantly (P<0.05) lower than that of TSB sham-vaccinated fish (FIG. 17).

Figure 18:
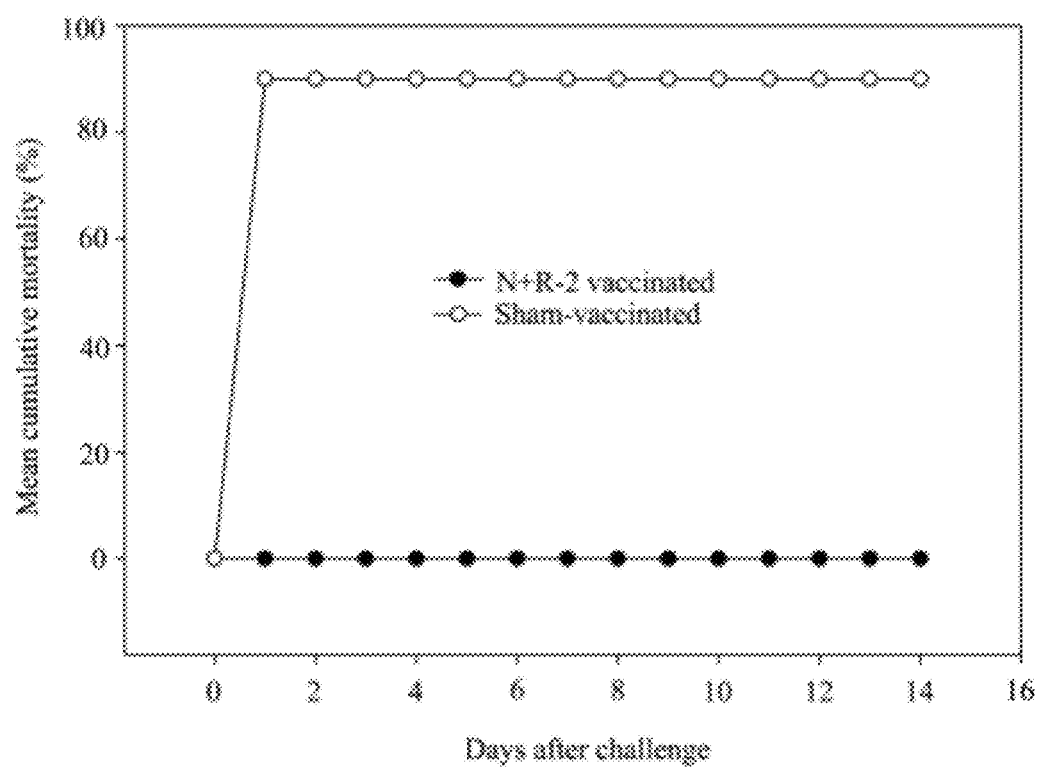
FIG. 18 is a graph showing daily mean percent cumulative mortality of *Aeromonas hydrophila* N+R−2 intraperitoneally injection vaccinated channel catfish challenged by virulent *Aeromonas hydrophila* AL09-73 (AL#2) through intraperitoneal injection. Daily mean percent cumulative mortalities were calculated from four vaccination doses/trials ($3.13\times10^4$, $6.25\times10^4$, $1.25\times10^5$, and $2.50\times10^5$CFU/fish). Data are represented as mean±S.D. from the four trials.

The TSB sham vaccinated fish challenged with the virulent parent strain AL09-73 of *Aeromonas hydrophila* had a mortality of approximately 90%. However, the fish vaccinated with the attenuated strain of N+R−2 at concentrations of $1.2 \times 10^6$, $1.2 \times 10^7$, and $1.2 \times 10^8$ CFU/fish all lived post challenge (Table 33). When N+R−2 vaccinated Nile tilapia were challenged by virulent AL09-73, cumulative mortalities of vaccinated fish, at vaccination doses of $1.2 \times 10^6$, $1.2 \times 10^7$, and $1.2 \times 10^8$ CFU/fish, were significantly (P<0.05) lower than that of TSB sham-vaccinated fish (FIG. 18).

Figure 19:
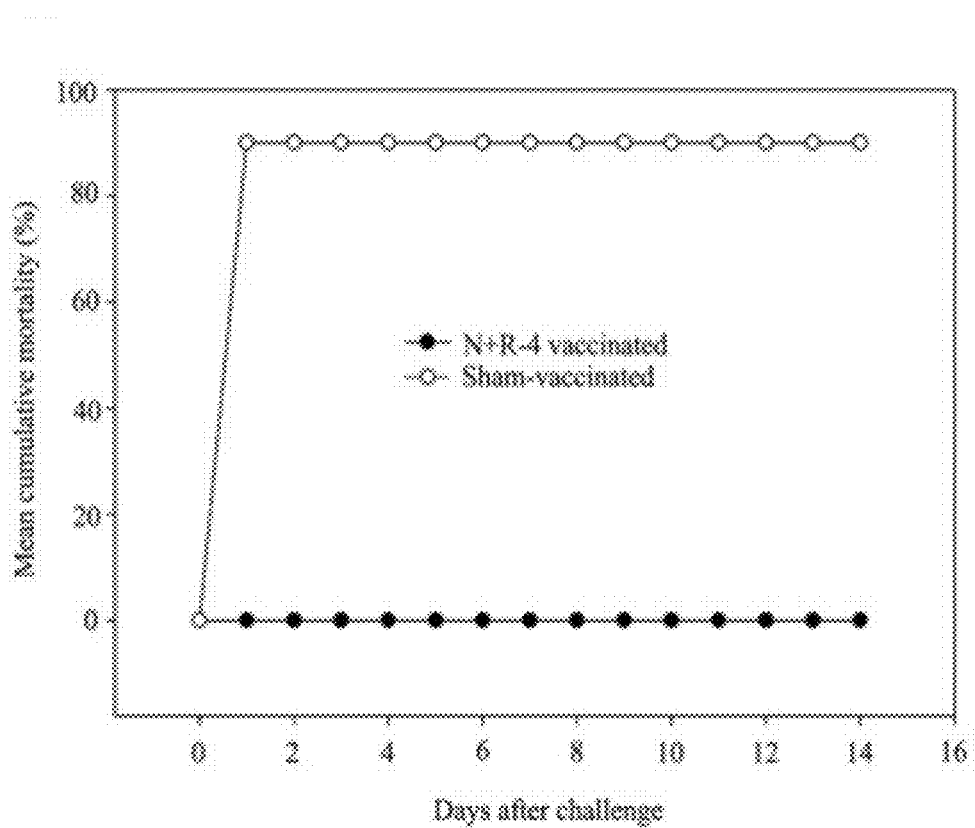
FIG. 19 is a graph showing the daily mean percent cumulative mortality of *Aeromonas hydrophila* N+R−2 intraperitoneally injection vaccinated Nile tilapia challenged by virulent *Aeromonas hydrophila* AL0973 (AL#2) through intraperitoneal injection. Daily mean percent cumulative mortalities were calculated from three vaccination doses/trials ($1.2\times10^6$, $1.2\times10^7$, and $1.2\times10^8$ CFU/fish). Data are represented as mean±S.D. from the three trials.

The TSB sham vaccinated fish challenged with the virulent parent strain AL09-71 of *Aeromonas hydrophila* had a mortality of approximately 90%. However, the fish vaccinated with the attenuated strain of N+R−4 all lived post challenge (Table 34). When N+R−4 vaccninated Nile tilapia were challenged by virulent AL09-71, cumulative mortalities of vaccinated fish, at vaccination doses of $1.3 \times 10^6$, $1.3 \times 10^7$, and $1.3 \times 10^8$ CFU/fish, were significantly (P<0.05) lower than that of TSB sham-vaccinated fish (FIG. 19).

TABLE 32

Cumulative mortality and relative percent survival (RPS) of IP vaccinated Nile tilapia challenged with AL09-72 virulent strain

| Vaccine group | Vaccination dose (CFU/fish) | Fish starting weight (g) | Challenge Dose (CFU/fish) | d.p.v.[a] | Mortality (%) | RPS[b] (%) |
|---|---|---|---|---|---|---|
| TSB[c] control | — | 10 | $3.2 \times 10^7$ | 28 | 92 | — |
| N + R − 1 | $1.4 \times 10^8$ | 10 | $3.2 \times 10^7$ | 28 | 15 | 84 |
| N + R − 1 | $1.4 \times 10^7$ | 10 | $3.2 \times 10^7$ | 28 | 24 | 74 |
| N + R − 1 | $1.4 \times 10^7$ | 10 | $3.2 \times 10^7$ | 28 | 64 | 30 |
| N + R − 1 | $1.4 \times 10^6$ | 10 | $3.2 \times 10^7$ | 28 | 68 | 26 |
| N + R − 1 | $1.4 \times 10^5$ | 10 | $3.2 \times 10^7$ | 28 | 80 | 13 |
| N + R − 1 | $1.4 \times 10^4$ | 10 | $3.2 \times 10^7$ | 28 | 92 | 0 |

[a] days post vaccination;
[b] relative percent survival;
[c] tryptic soy broth

TABLE 33

Cumulative mortality and relative percent survival (RPS) of IP vaccinated Nile tilapia challenged with AL09-73 virulent strain

| Vaccine group | Vaccination dose (CFU/fish) | Fish starting weight (g) | Challenge Dose (CFU/fish) | d.p.v.[a] | Mortality (%) | RPS[b] (%) |
|---|---|---|---|---|---|---|
| TSB[c] control | — | 15 | $1.2 \times 10^7$ | 28 | 90 | — |
| N + R − 2 | $1.2 \times 10^8$ | 15 | $1.2 \times 10^7$ | 28 | 0 | 100 |
| N + R − 2 | $1.2 \times 10^7$ | 15 | $1.2 \times 10^7$ | 28 | 0 | 100 |
| N + R − 2 | $1.2 \times 10^6$ | 15 | $1.2 \times 10^7$ | 28 | 0 | 100 |

[a] days post vaccination;
[b] relative percent survival;
[c] tryptic soy broth

TABLE 34

Cumulative mortality and relative percent survival (RPS) of IP vaccinated Nile tilapia challenged with AL09-71 virulent strain

| Vaccine group | Vaccination dose (CFU/fish) | Fish starting weight (g) | Challenge Dose (CFU/fish) | d.p.v.[a] | Mortality (%) | RPS[b] (%) |
|---|---|---|---|---|---|---|
| TSB[c] control | — | 15 | $1.3 \times 10^7$ | 28 | 90 | — |
| N + R − 4 | $1.3 \times 10^8$ | 15 | $1.3 \times 10^7$ | 28 | 0 | 100 |
| N + R − 4 | $1.3 \times 10^7$ | 15 | $1.3 \times 10^7$ | 28 | 0 | 100 |
| N + R − 4 | $1.3 \times 10^6$ | 15 | $1.3 \times 10^7$ | 28 | 0 | 100 |

[a] days post vaccination;
[b] relative percent survival;
[c] tryptic soy broth

All publications and patents mentioned in this specification are herein incorporated by reference to the same extent as if each individual publication or patent was specifically and individually indicated to be incorporated by reference.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention.

We claim:

1. An isolated attenuated *Streptococcus iniae* deposited with USDA ARS Patent Culture Collection, accession number NRRL B-50368.

2. A vaccine composition for protecting aquatic animals against infection by *Streptococcus iniae* comprising:
   a. an immunologically effective amount of an isolated attenuated *Streptococcus iniae* resistant to novobiocin or a novobiocin-like antibiotic and deposited with USDA ARS Patent Culture Collection, accession number NRRL B-50368, and
   b. a carrier.

* * * * *